US010851309B2

(12) United States Patent
Ramamurthy et al.

(10) Patent No.: US 10,851,309 B2
(45) Date of Patent: Dec. 1, 2020

(54) CONVERSION OF WASTE PLASTIC TO PROPYLENE AND CUMENE

(71) Applicant: SABIC Global Technologies B.V., Bergen op Zoom (NL)

(72) Inventors: Krishna Kumar Ramamurthy, Bengaluru (IN); Ravichander Bismillah Narayanaswamy, Bengaluru (IN); Venkata Ramanarayanan Ganapathy Bhotla, Bangalore (IN); Alexander Stanislaus, Bangalore (IN); Santosh Ganji, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 22 days.

(21) Appl. No.: 16/468,041

(22) PCT Filed: Jan. 3, 2018

(86) PCT No.: PCT/IB2018/050044
§ 371 (c)(1),
(2) Date: Jun. 10, 2019

(87) PCT Pub. No.: WO2018/127813
PCT Pub. Date: Jul. 12, 2018

(65) Prior Publication Data
US 2020/0017772 A1 Jan. 16, 2020

Related U.S. Application Data

(60) Provisional application No. 62/442,673, filed on Jan. 5, 2017.

(51) Int. Cl.
*C10G 1/00* (2006.01)
*C07C 2/66* (2006.01)
(Continued)

(52) U.S. Cl.
CPC ............... *C10G 1/002* (2013.01); *C07C 2/66* (2013.01); *C07C 6/04* (2013.01); *C10G 1/02* (2013.01);
(Continued)

(58) Field of Classification Search
None
See application file for complete search history.

(56) References Cited

U.S. PATENT DOCUMENTS 5,026,936 A   6/1991   Leyshon et al. ............. 585/315
6,916,448 B2  7/2005   Commereuc et al. ........ 585/324
(Continued)

FOREIGN PATENT DOCUMENTS

CN   101848880 B   7/2013
CN   103269791 B   9/2015
(Continued)

OTHER PUBLICATIONS

Angyal et al. "Petrochemical feedstock by thermal cracking of plastic waste." Journal of Analytical and Applied Pyrolysis, vol. 79, Issues 1-2, May 2007, pp. 409-414.
(Continued)

*Primary Examiner* — Philip Y Louie
(74) *Attorney, Agent, or Firm* — Norton Rose Fulbright US LLP

(57) ABSTRACT

A process for producing propylene and cumene comprising converting plastics to hydrocarbon liquid and pyrolysis gas in pyrolyzer; feeding hydrocarbon liquid to hydroprocessor to yield hydrocarbon product and first gas stream; introducing hydrocarbon product to second separator to produce first $C_6$ aromatics and refined product; feeding refined product to steam cracker to produce steam cracker product; introducing steam cracker product to third separator to produce second $C_6$ aromatics, third propylene stream, second $C_2$&$C_4$ unsatu-
(Continued)

rated stream, $C_{1-4}$ saturated gas, and balance hydrocarbons product; introducing pyrolysis gas and/or first gas stream to first separator to produce first propylene stream, first $C_2$&$C_4$ unsaturated stream, and saturated gas stream; feeding first and/or second $C_2$&$C_4$ unsaturated stream to metathesis reactor to produce second propylene stream; feeding first and/or second $C_6$ aromatics, and first, second, and/or third propylene stream to alkylation unit to produce cumene; and conveying balance hydrocarbons product to pyrolyzer and/or hydroprocessor.

20 Claims, 3 Drawing Sheets

(51) Int. Cl.

| | |
|---|---|
| *C07C 6/04* | (2006.01) |
| *C10G 1/02* | (2006.01) |
| *C10G 1/10* | (2006.01) |
| *C10G 69/06* | (2006.01) |
| *C10G 69/12* | (2006.01) |

(52) U.S. Cl.
CPC ............... *C10G 1/10* (2013.01); *C10G 69/06* (2013.01); *C10G 69/123* (2013.01); *C10G 2300/1003* (2013.01); *C10G 2400/20* (2013.01); *C10G 2400/30* (2013.01)

(56) References Cited

U.S. PATENT DOCUMENTS

| | | | |
|---|---|---|---|
| 2006/0089517 A1 | 4/2006 | Podrebarac et al. ......... 585/643 |
| 2008/0194890 A1 | 8/2008 | Brown ........................ 585/16 |
| 2009/0227823 A1 | 9/2009 | Huber et al. ................. 585/324 |
| 2016/0264874 A1 | 9/2016 | Narayanaswamy et al. |
| 2016/0264884 A1 | 9/2016 | Narayanaswamy et al. |
| 2016/0264885 A1* | 9/2016 | Narayanaswamy ... C10G 45/02 |
| 2016/0304788 A1* | 10/2016 | Sorensen ............. C08G 63/183 |

FOREIGN PATENT DOCUMENTS

| | | |
|---|---|---|
| JP | 2005154510 A | 6/2005 |
| JP | 2007302788 A | 11/2007 |
| JP | 4943816 B2 | 5/2012 |
| KR | 20140107559 A | 9/2014 |
| WO | WO2016030447 A1 | 3/1916 |
| WO | WO2007043738 A1 | 4/2007 |

OTHER PUBLICATIONS

International Search Report and Written Opinion from PCT/IB2018/050044 dated Apr. 9, 2018, 11 pages.
Lopez-Urionabarrenechea et al. "Upgrading of chlorinated oils coming from pyrolysis of plastic waste." Fuel Processing Technology, vol. 137, Sep. 2015, pp. 229-239.

\* cited by examiner

CONVERSION OF WASTE PLASTIC TO PROPYLENE AND CUMENE

This application is a national phase application under 35 U.S.C. § 371 of International Application No. PCT/IB2018/050044 filed Jan. 3, 2018, which claims priority to U.S. Provisional Patent Application No. 62/442,673 filed Jan. 5, 2017. The entire contents of each of the above-referenced disclosures is specifically incorporated by reference herein without disclaimer.

TECHNICAL FIELD

This disclosure relates to the production of high value products, such as olefins and aromatic hydrocarbons from mixed plastics via processes which include pyrolysis, hydroprocessing, steam cracking, alkylation, and olefin metathesis, wherein cumene and propylene are the preferred products.

BACKGROUND

Cumene is an important chemical intermediate, with almost all produced cumene being converted to cumene hydroperoxide, which is an intermediate in the synthesis of other industrially important chemicals, such as phenol and acetone, which can be further used in the production of bisphenol A. Current processes for producing cumene convert petroleum feedstock to benzene and propylene, which are then reacted to form cumene. The cumene produced from intermediates derived from petroleum feedstock is expensive, and as a result impacts the economics of the bisphenol A production process. Thus, there is an ongoing need to develop methods for producing cumene from feedstocks other than crude oil, for example from feedstocks derived from waste plastics.

BRIEF SUMMARY

Disclosed herein is a process for producing propylene and cumene comprising (a) converting a plastic waste to a hydrocarbon liquid stream and a pyrolysis gas stream in a pyrolysis unit, (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons, (c) introducing at least a portion of the hydrocarbon product to a second separating unit to produce a first $C_6$ aromatics stream and a refined product, wherein the refined product comprises $C_{5+}$ hydrocarbons other than $C_6$ aromatic hydrocarbons, and wherein the first $C_6$ aromatics stream comprises benzene, (d) feeding at least a portion of the refined product to a steam cracker to produce a steam cracker product, wherein an amount of olefins in the steam cracker product is greater than an amount of olefins in the refined product, (e) introducing at least a portion of the steam cracker product to a third separating unit to produce a second $C_6$ aromatics stream, a third propylene stream, a second $C_2$ and $C_4$ unsaturated stream, a $C_1$ to $C_4$ saturated gas stream and a balance hydrocarbons product, wherein the second $C_6$ aromatics stream comprises benzene, wherein the third propylene stream comprises propylene, wherein the second $C_2$ and $C_4$ unsaturated stream comprises ethylene and butylenes, and wherein the $C_1$ to $C_4$ saturated gas stream comprises hydrogen and $C_1$ to $C_4$ saturated hydrocarbons, (f) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons, (g) feeding at least a portion of the first $C_2$ and $C_4$ unsaturated stream and/or at least a portion of the second $C_2$ and $C_4$ unsaturated stream to a metathesis reactor to produce a second propylene stream, wherein the metathesis reactor comprises a metathesis catalyst, and wherein the second propylene stream comprises propylene, (h) feeding at least a portion of the first $C_6$ aromatics stream and/or at least a portion of the second $C_6$ aromatics stream, and at least a portion of the first propylene stream, at least a portion of the second propylene stream, at least a portion of the third propylene stream, or combinations thereof to an alkylation unit to produce cumene, wherein the alkylation unit comprises an alkylation catalyst, and (i) conveying at least a portion of the balance hydrocarbons product to the pyrolysis unit.

Also disclosed herein is a process for producing cumene comprising (a) converting a plastic waste to a hydrocarbon liquid stream and a pyrolysis gas stream in a pyrolysis unit, (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons, (c) introducing at least a portion of the hydrocarbon product to a second separating unit to produce a first $C_6$ aromatics stream, a $C_{7-8}$ aromatics stream, and a saturated hydrocarbons stream, wherein the first $C_6$ aromatics stream comprises benzene, wherein the $C_{7-8}$ aromatics stream comprises toluene, xylenes and ethylbenzene, and wherein the saturated hydrocarbons stream comprises $C_5+$ saturated hydrocarbons and $C_{9+}$ aromatic hydrocarbons, (d) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons, (h) feeding at least a portion of the first $C_6$ aromatics stream and at least a portion of the first propylene stream to an alkylation unit to produce cumene, wherein the alkylation unit comprises an alkylation catalyst, and (i) conveying at least a portion of the saturated hydrocarbons stream to the pyrolysis unit.

DETAILED DESCRIPTION

Figure 1A:
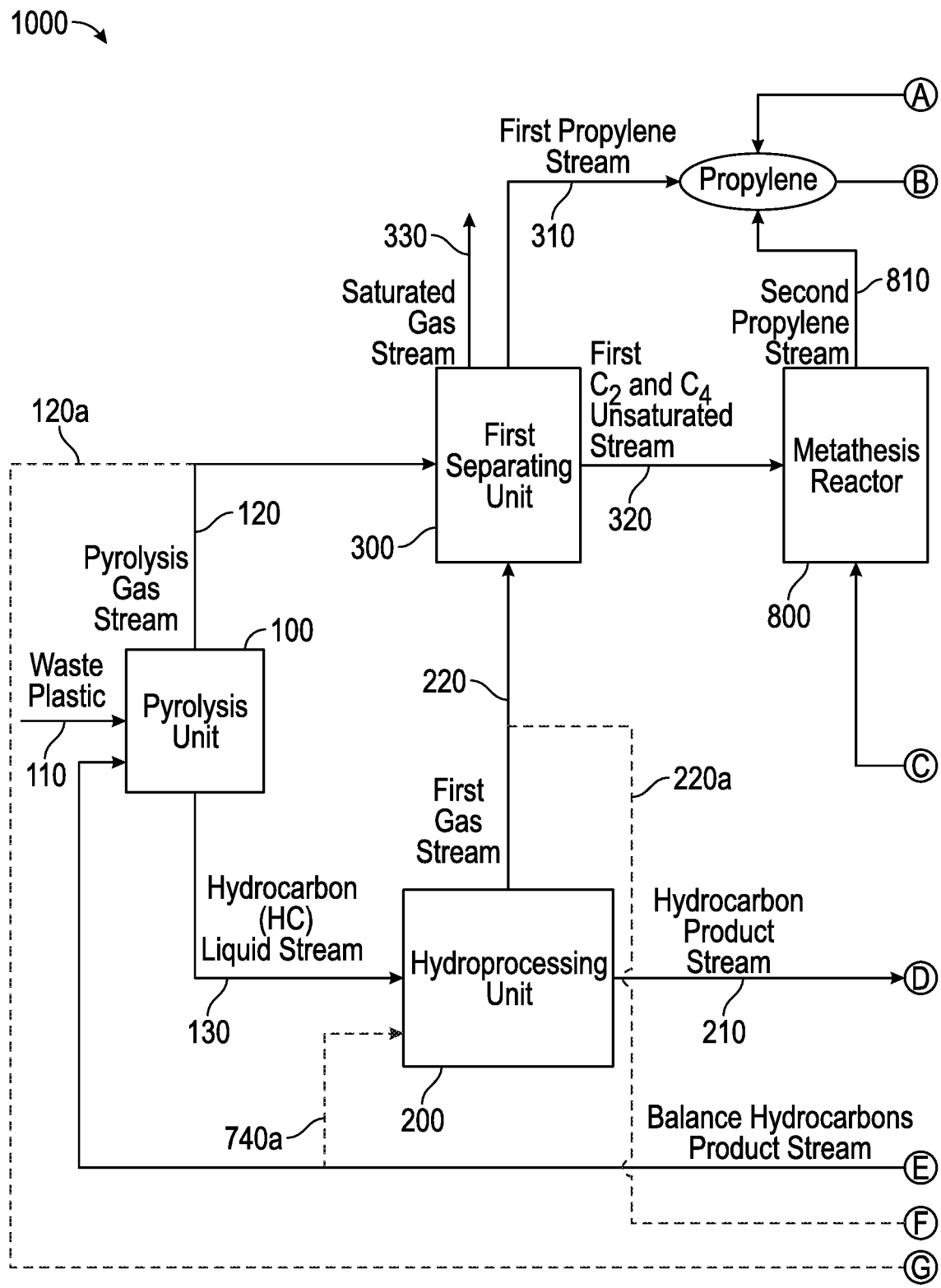
FIGS. 1A and 1B display a configuration of a system for producing propylene and cumene.

Disclosed herein are processes and systems for producing high value products such as cumene and propylene by processing plastic waste. The process may include conversion of waste plastic, which can be cracked or pyrolyzed by means of low temperature or high temperature pyrolysis, and by thermal or catalytic pyrolysis, wherein the composition of a pyrolysis product can be varied to maximize desired products by varying process conditions and catalysts. The plastic waste can be pyrolyzed to produce high yields of light gas olefins (i.e., ethylene, propylene, butylenes) and aromatics (i.e., benzene, toluene, xylenes (BTX), ethylbenzene (EB)), along with low yields of paraffins, iso-paraffins, and naphthenes. The pyrolysis can be configured to maximize propylene and/or aromatics, with high yields of BTX and EB. Maximizing propylene yields can also be achieved by employing a metathesis reaction to convert ethylene and butylenes streams to propylene, and further by employing a steam cracker to further crack a liquid stream from pyrolysis, thereby converting a portion of the liquid stream to light gas olefins. To maximize benzene production, the liquid obtained from low severity and/or high severity pyrolysis can be further hydrocracked and/or hydrotreated to reduce a boiling point of the heavies (e.g., heavies can be cracked to mostly $C_{10-}$ hydrocarbons), and to also saturate liquid olefins. Benzene can be further alkylated with propylene to form cumene.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "X or more" means that the named component is present in an amount of the value X, and values which are more than X.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

For purposes of the disclosure herein, the term "amount" refers to a weight % of a given component in a particular composition, based upon the total weight of that particular composition (e.g., the total weight of all components present in that particular composition), unless otherwise indicated.

Processes for producing cumene, for example from mixed plastics (e.g., plastic waste) are described in more detail with reference to FIGS. 1 and 2.

Figure 1B:
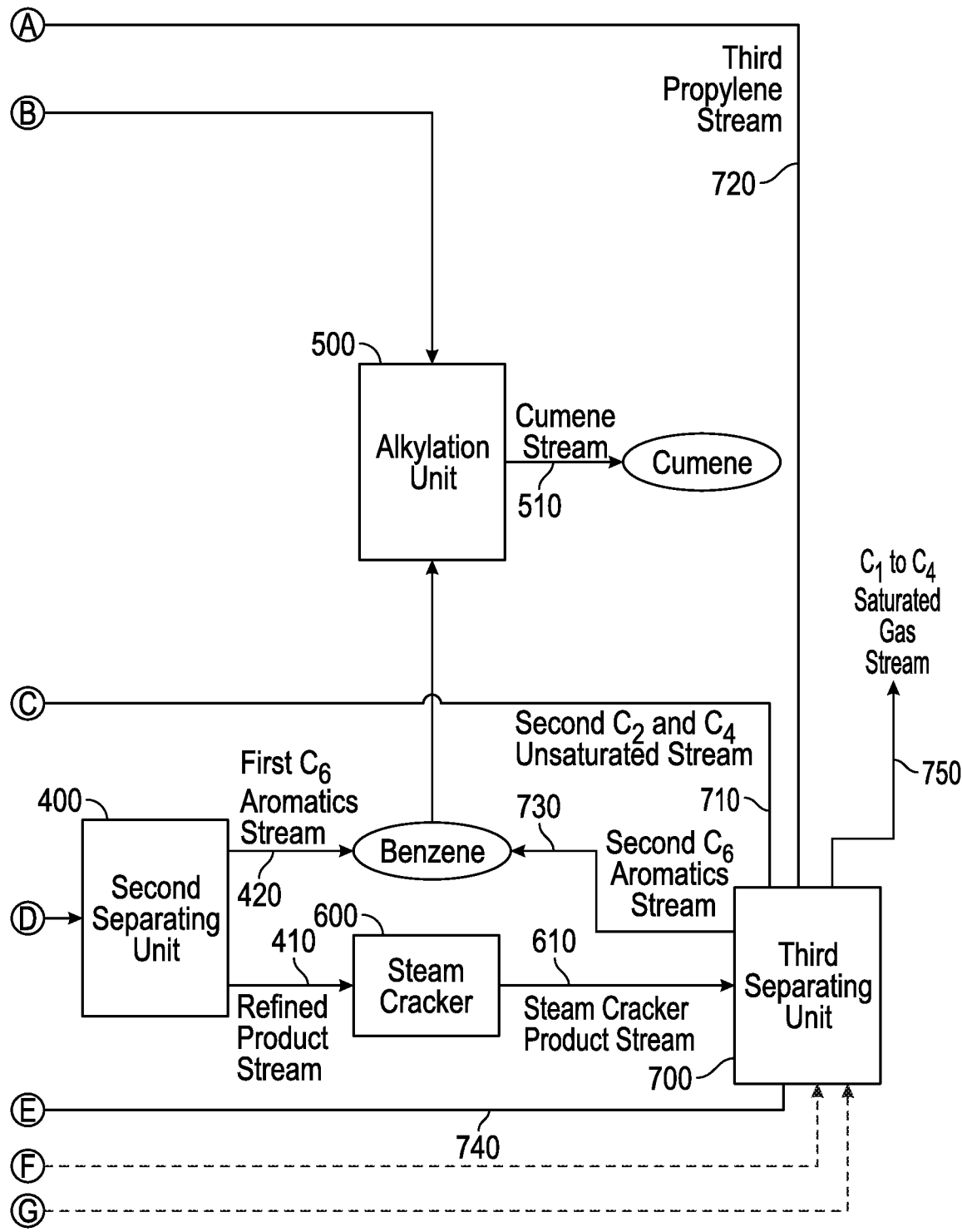

Referring to FIGS. 1A and 1B, a propylene and cumene production system 1000 is disclosed. The propylene and cumene production system 1000 generally comprises a pyrolysis unit 100; a hydroprocessing unit 200; a first separating unit or first separator 300; a second separating unit or second separator 400; an alkylation unit 500; a steam cracking unit 600; a third separating unit or third separator 700; and a metathesis reactor 800.

Figure 2:
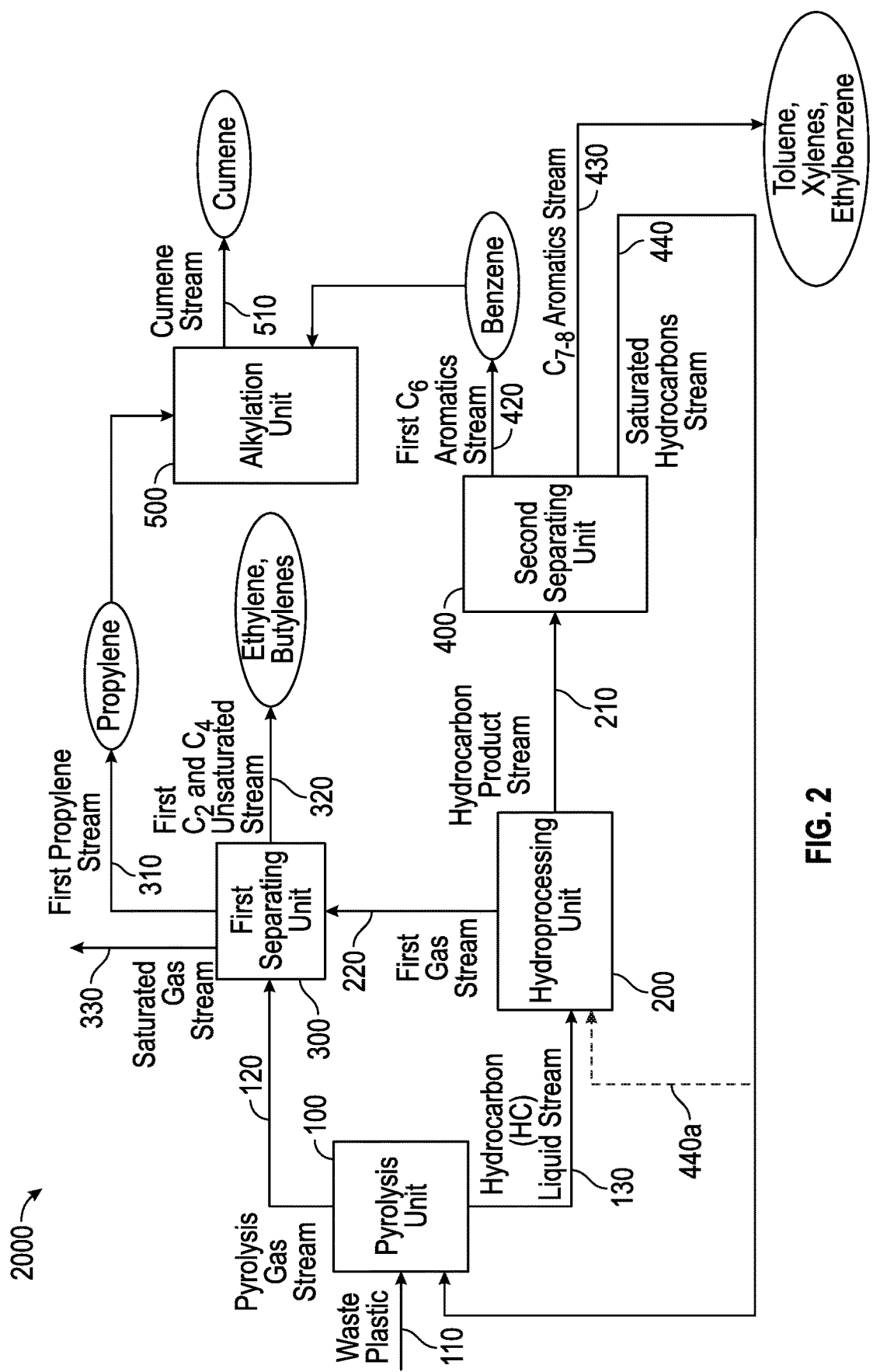
FIG. 2 displays a configuration of a system for producing cumene.

Referring to FIG. 2, a cumene production system 2000 is disclosed. The cumene production system 2000 generally comprises a pyrolysis unit 100; a hydroprocessing unit 200; a first separating unit or first separator 300; a second separating unit or second separator 400; and an alkylation unit 500.

While the current disclosure will be discussed in detail in the context of a single pyrolysis unit; a single hydroprocessing unit; a single alkylation unit; a single steam cracking unit; a single metathesis reactor; etc., it should be understood that any suitable configurations for a cumene production system can be used, wherein any given configuration for a cumene production system can comprise 1, 2, or more pyrolysis units; 1, 2, or more hydroprocessing units; 1, 2, or more alkylation units; 1,2, or more steam cracking units; 1, 2, or more metathesis reactors; etc.

A process for producing cumene can comprise a step of converting a plastic waste to a hydrocarbon liquid stream and a pyrolysis gas stream in a pyrolysis unit (e.g., pyrolyzer). The process can comprise introducing the waste plastics to a pyrolysis unit to produce a pyrolysis product, wherein the pyrolysis product comprises a gas phase and a liquid phase.

Mixed plastics (e.g., waste plastics) can be either placed in the pyrolysis unit 100 or fed to the pyrolysis unit 100 via waste plastic stream 110. In the pyrolysis unit 100, the waste plastic stream 110 is converted via pyrolysis to a pyrolysis product, wherein the pyrolysis product comprises a gas phase (e.g., pyrolysis gases, such as $C_1$ to $C_4$ gases, hydrogen ($H_2$), carbon monoxide (CO), carbon dioxide ($CO_2$), hydrochloric acid (HCl) gas, etc.) and a liquid phase (e.g., pyrolysis liquid).

Plastic waste which can be loaded into or fed to the pyrolysis unit 100 via waste plastic stream 110 may include post-consumer waste plastics, such as mixed plastic waste. Mixed plastics can comprise non-chlorinated plastics (e.g., polyolefins, polyethylene, polypropylene, polystyrene, copolymers, etc.), chlorinated plastics (e.g., polyvinylchloride (PVC), polyvinylidene chloride (PVDC), etc.), and the like, or mixtures thereof. Generally, waste plastics comprise long chain molecules or polymer hydrocarbons. Waste plastics as disclosed herein also include used tires.

The pyrolysis unit 100 may be any suitable vessel configured to convert waste plastics into gas phase and liquid phase products (e.g., simultaneously). The vessel may be configured for gas phase, liquid phase, vapor-liquid phase, gas-solid phase, liquid-solid phase, or slurry phase operation. The vessel may contain one or more beds of inert material or pyrolysis catalyst comprising sand, zeolite, alumina, a catalytic cracking catalyst, or combinations thereof. Generally, the pyrolysis catalyst is capable of transferring heat to the components subjected to the pyrolysis process in the pyrolysis unit 100. Alternatively, the pyrolysis unit 100 can be operated without any catalyst (e.g., pure thermal pyrolysis). The pyrolysis unit 100 may be operated adiabatically, isothermally, nonadiabatically, non-isothermally, or combinations thereof. The pyrolysis reactions of this disclosure may be carried out in a single stage or in multiple stages. For example, the pyrolysis unit 100 can be two reactor vessels fluidly connected in series.

In a configuration where the pyrolysis unit 100 comprises two vessels, the pyrolysis process may be divided into a first stage which is performed in a first vessel and in a second stage fluidly connected downstream of the first stage which is performed in the second vessel. As will be appreciated by one of skill in the art, and with the help of this disclosure, the second stage may enhance the pyrolysis of an intermediate pyrolysis product stream flowing from the first stage into the second stage, to yield a pyrolysis product flowing from the second stage. In some configurations, the first stage may utilize thermal cracking of the waste plastics, and the second stage may utilize thermal or catalytic cracking of the waste plastics to yield the pyrolysis product flowing from the second stage. Alternatively, the first stage may utilize catalytic cracking of the waste plastics, and the second stage may utilize thermal or catalytic cracking of the waste plastics to yield the pyrolysis product flowing from the second stage.

In some configurations, the pyrolysis unit 100 may include one or more equipment configured to convert mixed plastics into gas phase and liquid phase products. The one or more equipment may or may not contain an inert material or pyrolysis catalyst as described above. Examples of such equipment include one or more of heated extruders, heated rotating kiln, heated tank-type reactors, packed bed reactors, bubbling fluidized bed reactors, circulating fluidized bed reactors, empty heated vessels, enclosed heated surfaces where plastic flows down along the wall and cracks, vessels surrounded by ovens or furnaces, or any other suitable equipment offering a heated surface to assist in cracking.

The pyrolysis unit 100 can be configured to pyrolyze (e.g., crack), and in some aspects (e.g., where hydrogen is added to the pyrolysis unit 100), additionally hydrogenate components of the waste plastic stream 110 fed to the pyrolysis unit 100. Examples of reactions which may occur in the pyrolysis unit 100 include, but are not limited to isomerization of one or more normal paraffins to one or more i-paraffins, selective ring opening of one or more cycloparaffins to one or more i-paraffins, cracking of long chain length molecules to short chain length molecules, removal of heteroatoms from heteroatom-containing hydrocarbons (e.g., dechlorination), hydrogenation of coke generated in the process, or combinations thereof.

In one or more configurations of the pyrolysis unit 100, a head space purge gas can be utilized in all or a portion of the pyrolysis stage(s) (conversion of waste plastics to a liquid phase and/or gas phase products) to enhance cracking of plastics, produce valuable products, provide a feed for steam cracking, or combinations thereof. The head space purge gas may include hydrogen ($H_2$), $C_1$ to $C_4$ hydrocarbon gases (e.g., alkanes, methane, ethane, propane, butane, isobutane), inert gases (e.g., nitrogen ($N_2$), argon, helium, steam), and the like, or combinations thereof. The use of a head space purge gas assists in the dechlorination in the pyrolysis unit 100, when the waste plastic comprises chlorinated plastics. The head space purge gas may be introduced to the pyrolysis unit 100 to aid in the removal of volatiles entrained in the melted mixed plastics present in the pyrolysis unit 100.

A hydrogen ($H_2$) containing stream can be added to the pyrolysis unit 100 to enrich the pyrolysis unit environment with $H_2$, assist in stripping entrapped hydrogen chloride in the pyrolysis unit, provide a local environment rich in hydrogen in the pyrolysis melt or liquid, or combinations thereof; for example via a $H_2$ containing stream fed directly to the pyrolysis unit independently of the waste plastic stream 110. In some aspects, $H_2$ can also be introduced along with stream 110 to the pyrolysis unit 100, with adequate safety measures incorporated for hydrogen handling with plastics feed.

The pyrolysis unit 100 may facilitate any reaction of the components of the waste plastic stream 110 in the presence of, or with, hydrogen. Reactions may occur such as the addition of hydrogen atoms to double bonds of unsaturated molecules (e.g., olefins), resulting in saturated molecules (e.g., paraffins, i-paraffins, naphthenes). Additionally or alternatively, reactions in the pyrolysis unit 100 may cause a rupture of a bond of an organic compound, with a subsequent reaction and/or replacement of a heteroatom with hydrogen.

The use of hydrogen in the pyrolysis unit 100 can have beneficial effects of i) reducing the coke as a result of cracking, ii) keeping the catalyst used (if any) in the process in an active condition, iii) improving removal of chloride from stream 110 such that the pyrolysis product from pyrolysis unit 100 is substantially dechlorinated with respect to waste plastic stream 110, which minimizes the chloride removal requirement in units downstream of the pyrolysis unit 100, iv) hydrogenating of olefins, v) reducing diolefins in pyrolysis product, vi) helping operate the pyrolysis unit 100 at reduced temperatures for same levels of conversion of waste plastic stream 110 in the pyrolysis unit 100, or combinations of i)-vi).

The pyrolysis processes in the pyrolysis unit 100 may be low severity or high severity. Low severity pyrolysis processes may occur at a temperature of less than about 450° C., alternatively 250° C. to 450° C., alternatively 275° C. to 425° C., or alternatively 300° C. to 400° C., and may produce pyrolysis oils rich in mono- and di-olefins as well as a significant amount of aromatics. High severity pyrolysis processes may occur at a temperature of equal to or greater than about 450° C., alternatively 450° C. to 750° C., alternatively 500° C. to 700° C., or alternatively 550° C. to 650° C., and may produce pyrolysis oils rich in aromatics, as well as more gas products (as compared with low severity pyrolysis). As will be appreciated by one of skill in the art, and with the help of this disclosure, when it is desired to produce more gases (e.g., propylene) during pyrolysis, a high severity pyrolysis process is preferred over a low severity pyrolysis process.

An example of a pyrolysis process for waste plastics is disclosed in U.S. Pat. No. 8,895,790, which is incorporated by reference in its entirety. Another example of a pyrolysis process is disclosed in International Publication No. WO 2016/009333 A1, and U.S. patent application Ser. No. 15/085,445 filed Mar. 30, 2016, each of which is incorporated by reference in its entirety.

A pyrolysis product can be recovered as an effluent from the pyrolysis unit 100 and conveyed (e.g., flowed, for example via pumping, gravity, pressure differential, etc.) to a pyrolysis separating unit. The pyrolysis product can be separated in the pyrolysis separating unit into a pyrolysis gas stream 120 and a hydrocarbon liquid stream 130, wherein the pyrolysis gas stream 120 comprises at least a portion of the gas phase of the pyrolysis product, and wherein the hydrocarbon liquid stream 130 comprises at least a portion of the liquid phase of the pyrolysis product. The pyrolysis separating unit may comprise any suitable gas-liquid separator, such as a vapor-liquid separator, oil-gas separators, gas-liquid separators, degassers, deliqulizers, scrubbers, traps, flash drums, compressor suction drums, gravity separators, centrifugal separators, filter vane separators, mist eliminator pads, liquid-gas coalescers, distillation columns, and the like, or combinations thereof.

In some configurations, the pyrolysis separating unit can be a condenser which operates at conditions which condense a portion of the pyrolysis product into hydrocarbon liquids (e.g., liquid product) while leaving the hydrocarbon gases in the gas phase (e.g., gas product). A liquid product flows from the pyrolysis separating unit in hydrocarbon liquid stream 130, and a gas product flows from the pyrolysis separating unit in pyrolysis gas stream 120. The pyrolysis gas stream 120 can comprise $H_2$, $C_1$ to $C_4$ hydrocarbons, inert gases (e.g., nitrogen ($N_2$), argon, helium, steam, CO, $CO_2$), and the like, or combinations thereof.

The hydrocarbon liquid stream 130 can comprise paraffins, i-paraffins, olefins, naphthenes, aromatic compounds, organic chlorides, or combinations thereof. When the hydrocarbon liquid stream 130 comprises paraffins, i-paraffins, olefins, naphthenes, and aromatic compounds, the stream can be referred to as a PIONA stream; and when the hydrocarbon liquid stream 130 comprises paraffins, olefins, naphthenes, and aromatic compounds, the stream can be referred to as a PONA stream. In some aspects, the hydrocarbon liquid stream 130 can comprise a plastic pyrolysis oil and/or a tire pyrolysis oil.

As discussed herein, aspects of the processes disclosed herein contemplate hydrocracking of molecules, and in particular, heavy hydrocarbon molecules of the hydrocarbon liquid stream 130. As such, it is contemplated that at least a portion of the hydrocarbon liquid stream 130 comprises heavy hydrocarbon molecules (e.g., also referred to as heavy ends of pyrolysis oils). In an aspect, an amount of heavy hydrocarbon molecules in the hydrocarbon liquid stream 130 may be less than 10 wt. %, based on the total weight of the hydrocarbon liquid stream 130. Alternatively, the amount of the heavy hydrocarbon molecules in the hydrocarbon liquid stream 130 may be from 10 wt. % to 90 wt. %, based on the total weight of the hydrocarbon liquid stream 130. As will be described in more detail later herein, the heavy hydrocarbon molecules may include paraffins, i-paraffins, olefins, naphthenes, aromatic hydrocarbons, or combinations thereof. In some aspects, the heavy hydrocarbon molecules may include $C_{16}$ and larger hydrocarbons. Greater than 5, 10, 15, 20, 25, 30 wt. % or more of the heavy hydrocarbon molecules in the hydrocarbon liquid stream 130 is hydrocracked in the hydroprocessing unit 200.

Examples of paraffins which may be present in the hydrocarbon liquid stream 130 include, but are not limited to, $C_1$ to $C_{22}$ n-paraffins and i-paraffins. The paraffins can be present in the hydrocarbon liquid stream 130 in an amount of less than 10 wt. % based on the total weight of the hydrocarbon liquid stream 130. Alternatively, the paraffins can be present in the hydrocarbon liquid stream 130 in an amount of 10 wt. %, 20 wt. %, 30 wt. %, 40 wt. %, 50 wt. %, 60 wt. %, or more based on the total weight of the hydrocarbon liquid stream 130. While certain hydrocarbon liquid streams include paraffins of carbon numbers up to 22, the present disclosure is not limited to carbon number 22 as an upper end-point of the suitable range of paraffins, and the paraffins can include higher carbon numbers, e.g., 23, 24, 25, 26, 27, 28, 29, 30, 31, 32, 33, 34, 35, 36, 37, 38, 39, 40, and higher. In some aspects, at least a portion of the paraffins in the hydrocarbon liquid stream 130 comprises at least a portion of the heavy hydrocarbon molecules.

Examples of olefins which may be present in hydrocarbon liquid stream 130 include, but are not limited to, $C_2$ to $C_{10}$ olefins and combinations thereof. Where hydrogen is introduced to the pyrolysis unit 100, due to hydrogenation reactions in the pyrolysis unit 100, the olefins can be present in the hydrocarbon liquid stream 130 in an amount of less than 10 wt. %, based on the total weight of the hydrocarbon liquid stream 130. Alternatively, the olefins can be present in the hydrocarbon liquid stream 130 in an amount of 5 wt. %, 10 wt. %, 20 wt. %, 30 wt. %, 40 wt. %, or more based on the total weight of the hydrocarbon liquid stream 130. While certain hydrocarbon streams include olefins of carbon numbers up to 100, the present disclosure is not limited to carbon number 100 as an upper end-point of the suitable range of olefins, and the olefins can include higher carbon numbers, e.g., 11, 12, 13, 14, 15, 16, 17, 18, 19, 20, 21, 22, 23, 24, 25, 26, 27, 28, 29, 30, and higher. In some aspects, at least a portion of the one or more olefins in the hydrocarbon liquid stream 130 comprise at least a portion of the heavy hydrocarbon molecules. Alternatively, none of the heavy hydrocarbon molecules in the hydrocarbon liquid stream 130 are olefins.

In some aspects, the hydrocarbon liquid stream 130 comprises no olefins, e.g., the hydrocarbon liquid stream 130 is substantially free of olefins. In some aspects, the hydrocarbon liquid stream 130 comprises less than 1, 0.1, 0.01, or 0.001 wt. % olefins.

Examples of naphthenes which may be present in the hydrocarbon liquid stream 130 include, but are not limited to, cyclopentane, cyclohexane, cycloheptane, and cyclooctane. The naphthenes can be present in the hydrocarbon liquid stream 130 in an amount of less than 10 wt. %, based on the total weight of the hydrocarbon liquid stream 130. Alternatively, the naphthenes can be present in the hydrocarbon liquid stream 130 in an amount of 10 wt. %, 20 wt. %, 30 wt. %, 40 wt. %, or more based on the total weight of the hydrocarbon liquid stream 130. While certain hydrocarbon streams include naphthenes of carbon numbers up to 8, the present disclosure is not limited to carbon number 8 as an upper end-point of the suitable range of naphthenes, and the naphthenes can include higher carbon numbers, e.g., 9, 10, 11, 12, 13, 14, 15, 16, 17, 18, 19, 20, 21, 22, 23, 24, 25, 26, 27, 28, 29, 30, and higher. In some aspects, at least a portion of the naphthenes in the hydrocarbon liquid stream 130 comprises at least a portion of the heavy hydrocarbon molecules.

The hydrocarbon liquid stream 130 may comprise aromatic hydrocarbons with carbon numbers of 6, 7, 8, 9, 10, 11, 12, 13, 14, 15, 16, 17, 18, 19, 20, 21, 22, 23, 24, 25, 26, 27, 28, 29, 30, and higher. In an aspect, the aromatic hydrocarbons carbon number can be as high as 22. Nonlimiting examples of aromatic hydrocarbons suitable for use in the present disclosure as part of the hydrocarbon liquid stream 130 include benzene, toluene, xylenes, ethylbenzene, propylbenzenes, trimethylbenzenes, tetramethylbenzenes, butylbenzenes, dimethylnaphthalene, biphenyl, and the like, or combinations thereof. The aromatic hydrocarbons can be present in the hydrocarbon liquid stream 130 in an amount of 5 wt. %, 10 wt. %, 15 wt. %, 20 wt. %, 25 wt. %, 30 wt. %, 35 wt. %, 40 wt. %, 50 wt. %, 60 wt. %, or more based on the total weight of the hydrocarbon liquid stream 130. In some aspects, at least a portion of the aromatic hydrocarbons in the hydrocarbon liquid stream 130 comprises at least a portion of the heavy hydrocarbon molecules.

A process for producing cumene can comprise a step of contacting at least a portion of the hydrocarbon liquid stream 130 with a hydroprocessing catalyst in the presence of hydrogen in the hydroprocessing unit 200 to yield a hydrocarbon product stream 210 and a first gas stream 220, wherein the hydrocarbon product stream 210 comprises $C_5$+ hydrocarbons. The first gas stream 220 can comprise $H_2$, $C_1$ to $C_4$ hydrocarbons, inert gases (e.g., nitrogen ($N_2$), argon, helium, steam, CO, $CO_2$), and the like, or combinations thereof.

The hydroprocessing unit 200 can be any suitable hydroprocessing reactor (e.g., hydroprocessor), such as a hydrocracker, a catalytic cracker operated in hydropyrolysis mode, a fluid catalytic cracker operated in hydropyrolysis mode, a hydrotreater, and the like, or combinations thereof. The hydroprocessing unit 200 is configured to hydrocrack long chain molecules (e.g., heavy hydrocarbon molecules contained in the hydrocarbon liquid stream 130), hydrogenate and dechlorinate (where stream 130 contains chloride) components of the hydrocarbon liquid stream 130 fed to the hydroprocessing unit 200. In the hydroprocessing unit 200, the hydrocarbon liquid stream 130 is contacted with a hydroprocessing catalyst in the presence of hydrogen to yield the hydrocarbon product stream 210. It is contemplated that the hydrocarbon liquid stream 130 may be contacted with the hydroprocessing catalyst in upward flow, downward flow, radial flow, or combinations thereof, with or without a staged addition of hydrocarbon liquid stream 130, a $H_2$ stream, or combinations thereof.

The hydroprocessing unit 200 may be any vessel configured to contain the hydroprocessing catalyst disclosed herein. The vessel may be configured for gas phase, liquid phase, vapor-liquid phase, gas-liquid-solid phase, or slurry phase operation. The hydroprocessing unit 200 may include one or more beds of the hydroprocessing catalyst configured as a fixed bed, a fluidized bed, a moving bed, an ebullated bed, a slurry bed, or combinations thereof. The hydroprocessing unit 200 may be operated adiabatically, isothermally, nonadiabatically, non-isothermally, or combinations thereof. In an aspect, the hydroprocessing unit 200 may comprise one or more vessels.

The hydroprocessing unit 200 may facilitate any reaction of the components of the hydrocarbon liquid stream 130 in the presence of, or with, hydrogen. Reactions may occur as the addition of hydrogen atoms to double bonds of unsaturated molecules (e.g., olefins, aromatic compounds), resulting in saturated molecules (e.g., paraffins, i-paraffins, naphthenes). Additionally, reactions in the hydroprocessing unit 200 may cause a rupture of a bond of an organic compound, resulting in "cracking" of a hydrocarbon molecule into two or more smaller hydrocarbon molecules, or resulting in a subsequent reaction and/or replacement of a heteroatom with hydrogen. Examples of reactions which may occur in the hydroprocessing unit 200 include, but are not limited to, the hydrogenation of olefins, removal of heteroatoms from heteroatom-containing hydrocarbons (e.g., dechlorination), hydrocracking of large paraffins or i-paraffins to smaller hydrocarbon molecules, hydrocracking of aromatic hydrocarbons to smaller cyclic or acyclic hydrocarbons, conversion of one or more aromatic compounds to one or more cycloparaffins, isomerization of one or more normal paraffins to one or more i-paraffins, selective ring opening of one or more cycloparaffins to one or more i-paraffins, or combinations thereof.

In an aspect, contacting the hydrocarbon liquid stream 130 with the hydroprocessing catalyst in the presence of hydrogen yields $C_1$ to $C_4$ gases and $C_5+$ ($C_5$ and heavier) liquid hydrocarbons. When the waste plastic stream 110 contains chloride, it is contemplated that dechlorination using the hydroprocessing catalyst as described herein can be performed in the hydroprocessing unit 200 without the use of chlorine sorbents, without addition of $Na_2CO_3$ in an effective amount to function as a dechlorinating agent, or both.

The hydroprocessing catalyst may be any catalyst used for hydrogenation (e.g., saturation) of olefins and aromatic hydrocarbons (e.g., a commercially available hydrotreating catalyst). The hydroprocessing catalyst can comprise a cobalt and molybdenum catalyst (Co—Mo catalyst) on an alumina support, a nickel and molybdenum catalyst (Ni—Mo catalyst) on an alumina support, a tungsten and molybdenum catalyst (W—Mo catalyst) on an alumina support, cobalt and molybdenum oxides on an alumina support, nickel and molybdenum oxides on an alumina support, tungsten and molybdenum oxides on an alumina support, cobalt and molybdenum sulphides on an alumina support, nickel and molybdenum sulphides on an alumina support, tungsten and molybdenum sulphides on an alumina support, a zeolite comprising one or more metals, and the like, or combinations thereof. Other catalysts suitable for use as the hydroprocessing catalyst may include platinum and palladium catalyst (Pt—Pd catalyst) on an alumina support, nickel sulphides suitable for slurry processing, molybdenum sulphides suitable for slurry processing, and the like, or combinations thereof. The zeolites can comprise ZSM-5, ZSM-11, Y, high-silica Y, USY, and the like, or combinations thereof. Each metal of the one or more metals of the zeolite can be independently selected from the group consisting of cobalt, molybdenum, tungsten, nickel, titanium, copper, magnesium, tin, iron, zinc, tungsten, vanadium, gallium, calcium, manganese, ruthenium and rhenium.

In configurations where the hydrocarbon liquid stream 130 comprises one or more sulphides and one or more chloride compounds, contacting the hydrocarbon liquid stream 130 with the hydroprocessing catalyst acts to activate the hydroprocessing catalyst by sulphiding and to acidify the hydroprocessing catalyst by chlorinating. Continuously contacting the hydroprocessing catalyst with the hydrocarbon liquid stream 130 containing one or more sulphides, one or more chloride compounds, or both, may maintain catalyst activity on a continuous basis. For purposes of the disclosure herein, the term "catalyst activity" or "catalytic activity" with respect to the hydroprocessing catalyst refers to the ability of the hydroprocessing catalyst to catalyze hydroprocessing reactions, such as hydrocracking reactions, hydrodechlorination reactions, etc.

A hydrogen stream can be added to the hydroprocessing unit 200 to enrich the hydroprocessing unit environment with $H_2$, for example via a stream fed directly to the hydroprocessing unit independently of the hydrocarbon liquid stream 130. Additionally or alternatively, a $H_2$ containing stream can be added to the hydrocarbon liquid stream 130 before entering the hydroprocessing unit 200. The rate of hydrogen addition to the hydroprocessing unit 200 is generally sufficient to achieve the hydrogen to hydrocarbon ratios disclosed herein.

The disclosed hydroprocessing unit 200 may operate at various process conditions. For example, contacting the hydrocarbon liquid stream 130 with the hydroprocessing catalyst in the presence of hydrogen may occur in the hydroprocessing unit 200 at a temperature of from 250° C. to 600° C.; alternatively, 275° C. to 550° C.; or alternatively, 300° C. to 500° C. The temperature in the hydroprocessing unit 200 can be attained by using a feed (e.g., hydrocarbon liquid stream 130) pre-heating furnace and/or feed-hydroprocessing unit effluent heat exchangers. Contacting the hydrocarbon liquid stream 130 with the hydroprocessing catalyst in the presence of hydrogen may occur in the hydroprocessing unit 200 at a pressure of 1 barg to 200 barg, alternatively, 10 barg to 150 barg, or alternatively, 20 barg to 60 barg. Contacting the hydrocarbon liquid stream 130 with the hydroprocessing catalyst in the presence of hydrogen may occur in the hydroprocessing unit 200 at a weight hourly space velocity (WHSV) of between 0.1 $hr^{-1}$ to 10 $hr^{-1}$; or alternatively, 1 $hr^{-1}$ to 3 $hr^{-1}$. Contacting the hydrocarbon liquid stream 130 with the hydroprocessing catalyst in the presence of hydrogen may occur in the hydroprocessing unit 200 at a hydrogen to hydrocarbon ($H_2$/HC) flow ratio of from 10 NL/L to 3,000 NL/L; or alternatively, from 200 NL/L to 800 NL/L.

In some configurations, the hydroprocessing unit 200 can be a mild hydrocracking unit, such as a mild hydrocracker used in refining operations, wherein the hydroprocessing unit 200 can operate at pressures of up to 100 barg and at temperatures of up to 430° C. As will be appreciated by one of skill in the art, and with the help of this disclosure, the hydroprocessing unit 200 could operate at lower pressures to economize on hydrogen consumption and to preserve mono-ring aromatics (and only saturate di- and poly-aromatics, and olefins). Generally, mild hydrocracking units can saturate liquid olefins introduced to the mild hydrocracking unit, as well as reduce the heavies by selective cracking and hydrogenation, such that at least a portion of the mono-ring aromatics can be preserved. As will be appreciated by one of skill in the art, and with the help of this disclosure, since plastic pyrolysis oils are rich in hydrogen content compared to petroleum residues, it is possible to carry out the hydroprocessing at lower pressures of less than 100 barg. Further, as will be appreciated by one of skill in the art, and with the help of this disclosure, higher pressures of more than 100 barg can also be used with plastic pyrolysis oils.

In some aspects, the hydroprocessing unit 200 can further comprise a hydrodealkylating unit, wherein the hydrodealkylating unit can comprise a hydrodealkylating catalyst. The hydrodealkylating unit can be any suitable hydroprocessing reactor, such as a hydrocracker, a catalytic cracker operated in hydropyrolysis mode, a fluid catalytic cracker operated in hydropyrolysis mode, a hydrotreater, a hydrodealkylating reactor, and the like, or combinations thereof. The hydrodealkylating unit can be configured to hydrodealkylate, and in some configurations, additionally hydrocrack, dechlorinate and hydrogenate components of the hydrocarbon liquid stream 130.

The hydrodealkylating unit may be any vessel configured to contain the hydrodealkylating catalyst disclosed herein. The vessel may be configured for gas phase, liquid phase, vapor-liquid phase, gas-solid phase, gas-liquid-solid phase, or slurry phase operation. The hydrodealkylating unit may include one or more beds of the hydrodealkylating catalyst configured as a fixed bed, a fluidized bed, a moving bed, an ebullated bed, a slurry bed, or combinations thereof. The hydrodealkylating unit may be operated adiabatically, isothermally, nonadiabatically, non-isothermally, or combinations thereof. In an aspect, the hydrodealkylating unit may comprise one or more vessels.

The hydrodealkylating unit may facilitate any suitable reaction of the components of the hydrocarbon liquid stream 130 in the presence of, or with, hydrogen. Reactions in the hydrodealkylating unit include a hydrodealkylation reaction of $C_9+$ aromatic hydrocarbons, wherein the $C_9+$ aromatic hydrocarbons in the presence of hydrogen form lower molecular weight aromatic hydrocarbons (e.g., $C_{6-8}$ aromatic hydrocarbons) and alkanes. For example, trimethylbenzenes can undergo a hydrodealkylation reaction to produce xylenes and methane. Other reactions may occur in the hydrodealkylating unit, such as the addition of hydrogen atoms to double bonds of unsaturated molecules (e.g., olefins, aromatic compounds), resulting in saturated molecules (e.g., paraffins, i-paraffins, naphthenes). Additionally, reactions in the hydrodealkylating unit may cause a rupture of a bond of an organic compound, resulting in "cracking" of a hydrocarbon molecule into two or more smaller hydrocarbon molecules, or resulting in a subsequent reaction and/or replacement of a heteroatom with hydrogen. Examples of reactions which may occur in the hydrodealkylating unit include, but are not limited to, hydrodealkylation of $C_9+$ aromatic hydrocarbons, the hydrogenation of olefins, removal of heteroatoms from heteroatom-containing hydrocarbons (e.g., dechlorination), hydrocracking of large paraffins or i-paraffins to smaller hydrocarbon molecules, hydrocracking of aromatic hydrocarbons to smaller cyclic or acyclic hydrocarbons, conversion of one or more aromatic compounds to one or more cycloparaffins, isomerization of one or more normal paraffins to one or more i-paraffins, selective ring opening of one or more cycloparaffins to one or more i-paraffins, or combinations thereof.

The hydrodealkylating catalyst may be any suitable catalyst used for hydrogenation (e.g., saturation) of olefins and aromatic hydrocarbons (e.g., a commercially available hydrotreating catalyst), such as the catalysts described herein for the hydroprocessing catalyst. Additionally, the hydrodealkylating catalyst may be any suitable hydrodealkylation catalyst (e.g., a commercially available hydrodealkylation catalyst), such as chromium oxides on an alumina support, chromium oxides on a silica support, molybdenum oxides on an alumina support, molybdenum oxides on a silica support, platinum on an alumina support, platinum on a silica support, platinum oxides on an alumina support, platinum oxides on a silica support, and the like, or combinations thereof.

The hydrocarbon product stream 210 comprises $C_5+$ liquid hydrocarbons, wherein the $C_5+$ liquid hydrocarbons comprise heavy hydrocarbon molecules. An amount of heavy hydrocarbon molecules in the hydrocarbon product stream 210 is less than an amount of heavy hydrocarbon molecules in the hydrocarbon liquid stream 130 due to hydrocracking of at least a portion of heavy hydrocarbon molecules from the hydrocarbon liquid stream during the step of contacting the hydrocarbon liquid stream 130 with a hydroprocessing catalyst in the presence of hydrogen in the hydroprocessing unit 200.

In some aspects, the hydrocarbon product stream 210 can comprise equal to or greater than about 90 wt. %, alternatively equal to or greater than about 92.5 wt. %, or alternatively equal to or greater than about 95 wt. % $C_{10}-$ hydrocarbons, based on the total weight of the hydrocarbon product stream 210. As will be appreciated by one of skill in the art, and with the help of this disclosure, the conditions inside the hydroprocessing unit 200 can be such that the produced hydrocarbon product comprises mostly $C_{10}-$ hydrocarbons.

The hydrocarbon product stream 210 can be characterized by an olefin content that is lower than an olefin content of the hydrocarbon liquid stream 130. In some aspects, the hydrocarbon product stream 210 can be characterized by an olefin content of less than about 1, 0.1, 0.01, or 0.001 wt. % olefins, based on the total weight of the hydrocarbon product stream 210.

The hydrocarbon product stream 210 can be characterized by a boiling point that is lower than the boiling point of the hydrocarbon liquid stream 130. In an aspect, equal to or greater than about 97 wt. %, alternatively 98 wt. %, or alternatively 99.9 wt. % of the hydrocarbon product stream 210 is characterized by a boiling point of less than about 370° C., or alternatively less than about 350° C. In some aspects, the hydrocarbon product stream 210 is characterized by a boiling point of less than about 370° C.

The hydrocarbon product stream 210 can be characterized by a chloride content that is lower than a chloride content of the hydrocarbon liquid stream 130, wherein a decrease in chloride content results from dehydrochlorination of the hydrocarbon liquid stream 130 during the step of contacting the hydrocarbon liquid stream 130 with a hydroprocessing catalyst in the presence of hydrogen in the hydroprocessing unit 200. The hydrocarbon product stream 210 can comprise one or more chloride compounds in an amount of less than about 10 parts per million weight (ppmw) chloride, alternatively less than about 5 ppmw chloride, or alternatively less than about 3 ppmw chloride, based on the total weight of the hydrocarbon product stream 210.

Referring to FIGS. 1A and 1B, a process for producing cumene can comprise a step of introducing at least a portion of the hydrocarbon product stream 210 to the second separating unit 400 to produce a first $C_6$ aromatics stream 420 and a refined product stream 410, wherein the first $C_6$ aromatics stream 420 comprises benzene.

The refined product stream 410 comprises $C_{5+}$ hydrocarbons other than $C_6$ aromatic hydrocarbons. In an aspect, the refined product stream 410 comprises $C_5+$ saturated hydrocarbons and $C_{7+}$ aromatic hydrocarbons, such as $C_7$ aromatic hydrocarbons, $C_8$ aromatic hydrocarbons, $C_9$ aromatic hydrocarbons, $C_{10}$ aromatic hydrocarbons, or combinations thereof. As will be appreciated by one of skill in the art, and with the help of this disclosure, the $C_{5+}$ hydrocarbons of the refined product stream 410 (i) exclude $C_6$ aromatic hydrocarbons, such as benzene; (ii) exclude $C_{5+}$ olefins; (iii) include $C_{5+}$ paraffins, iso-paraffins and naphthenes; and (iv) include $C_{7+}$ aromatic hydrocarbons.

The second separating unit 400 can comprise any suitable separating unit that is configured to recover the first $C_6$ aromatics stream 420 from the hydrocarbon product stream 210. For example, the second separating unit 400 can employ selective adsorption, selective absorption, extractive distillation, and the like, or combinations thereof.

In some aspects, at least a portion of the refined product stream 410 can be further separated into a $C_{7-8}$ aromatics stream 430 and a saturated hydrocarbons stream 440, wherein the $C_{7-8}$ aromatics stream 430 comprises toluene, xylenes and ethylbenzene, and wherein the saturated hydrocarbons stream 440 comprises $C_5+$ saturated hydrocarbons and $C_{9+}$ aromatic hydrocarbons. The saturated hydrocarbons stream 440 can generally comprise a small amount of $C_{9-10}$ aromatic hydrocarbons (e.g., $C_9$ aromatic hydrocarbons, $C_{10}$ aromatic hydrocarbons, or combinations thereof). As will be appreciated by one of skill in the art, and with the help of this disclosure, the $C_{5+}$ saturated hydrocarbons of the saturated hydrocarbons stream 440 (i) exclude $C_{6-8}$ aromatic hydrocarbons; (ii) exclude $C_{5+}$ olefins; and (iii) include $C_{5+}$ paraffins, iso-paraffins and naphthenes.

In some aspects, the process for producing cumene can further comprise recovering at least a portion of the xylenes from the $C_{7-8}$ aromatics stream 430. An overall xylenes yield can be equal to or greater than about 12 wt. %, alternatively equal to or greater than about 15 wt. %, or alternatively equal to or greater than about 20 wt. %.

In some configurations, such as the configuration of the cumene production system 2000, the $C_{7-8}$ aromatics stream 430 and the saturated hydrocarbons stream 440 can be recovered from the second separating unit 400, without recovering a refined product stream 410 from the second separating unit 400. In such configurations, and as will be appreciated by one of skill in the art, and with the help of this disclosure, the components of the refined product stream 410 are further separated in the second separating unit 400 into the $C_{7-8}$ aromatics stream 430 and the saturated hydrocarbons stream 440.

In other configurations, the refined product stream 410 can be further separated into the $C_{7-8}$ aromatics stream 430 and the saturated hydrocarbons stream 440 in a separating unit other than the second separating unit 400. For example, at least a portion of the useful aromatics (e.g., $C_{7-8}$ aromatics) can be recovered from the refined product stream 410 prior to introducing to the steam cracker 600.

In some aspects, at least a portion of the saturated hydrocarbons stream 440 can be conveyed to the pyrolysis unit 100. In other aspects, at least a portion 440a of the saturated hydrocarbons stream can be conveyed to the hydroprocessing unit 200. In yet other aspects, at least a portion of the saturated hydrocarbons stream can be conveyed to the steam cracker 600.

A process for producing cumene can comprise a step of feeding at least a portion of the refined product stream 410 and/or saturated hydrocarbon stream 440 to the steam cracker 600 to produce a steam cracker product stream 610, wherein an amount of olefins in the steam cracker product stream 610 is greater than an amount of olefins in the refined product stream 410 and/or saturated hydrocarbon stream 440, respectively. The refined product stream 410 and/or saturated hydrocarbon stream 440 meet steam cracker feed requirements for chloride content, olefin content, and boiling end point.

Generally, steam cracking is a process in which saturated hydrocarbons are broken down into smaller, often unsaturated, hydrocarbons (i.e., olefins). In steam cracking, a hydrocarbon feed stream, such as the refined product stream 410 and/or saturated hydrocarbon stream 440, can be diluted with steam and briefly heated in a furnace or cracker, such as steam cracker 600, in the absence of oxygen. Typically, a steam cracking reaction temperature is very high, at around 800° C. or more, and residence times can be short (e.g., on the order of milliseconds) to improve yield. After reaching the cracking temperature, the cracked gas mixture can be quickly quenched to stop the reaction, for example in a transfer line heat exchanger or inside a quenching header using quench oil.

Steam cracker 600 generally has feed specification requirements, e.g., requires a dechlorinated feed with low chloride content, a low olefin content and with a specific boiling end point or boiling point distribution.

The steam cracker 600 cracks molecules or cleaves at elevated temperatures carbon-carbon bonds of the components in the refined product stream 410 and/or saturated hydrocarbon stream 440 in the presence of steam to yield high value products.

As will be appreciated by one of skill in the art, and with the help of this disclosure, the composition of the steam cracking product depends on reactor parameters (e.g., temperature, residence time, hydrocarbon to steam ratio, etc.), as well as on the composition of the feed to the cracker. Heavier hydrocarbons, such as in liquid feed streams (e.g., refined product stream 410 and/or saturated hydrocarbon stream 440) can produce a substantial amount of aromatic hydrocarbons (e.g., $C_6$-$C_8$ aromatic hydrocarbons), as well as olefins (e.g., light gas olefins, ethylene, propylene, butylenes, butadiene, etc.).

A steam cracker product stream 610 comprising high value products can be recovered from the steam cracker 600, wherein the high value products comprise ethylene, propylene, butylenes, butadiene, aromatic compounds, and the like, or combinations thereof.

The steam cracker product stream 610 can be characterized by an olefin content that is greater than an olefin content of the refined product stream 410 and/or saturated hydrocarbon stream 440. In some aspects, the steam cracker product stream 610 can be characterized by an olefin content of equal to or greater than about 50 wt. % olefins, based on the total weight of the steam cracker product stream 610.

Referring to FIGS. 1A and 1B, a process for producing cumene can comprise a step of introducing at least a portion of the steam cracker product stream 610, at least a portion 120a of the pyrolysis gas stream, at least a portion 220a of the first gas stream, or combinations thereof to the third separating unit 700 to produce a second $C_2$ and $C_4$ unsaturated stream 710, a third propylene stream 720, a second $C_6$ aromatics stream 730, a balance hydrocarbons product stream 740, and a $C_1$ to $C_4$ saturated gas stream 750, wherein the second $C_2$ and $C_4$ unsaturated stream 710 comprises ethylene and butylenes, wherein the third propylene stream 720 comprises propylene, wherein the second $C_6$ aromatics stream 730 comprises benzene, wherein the $C_1$ to $C_4$ saturated gas stream 750 comprises hydrogen and $C_1$ to $C_4$ saturated hydrocarbons, and wherein the balance hydrocarbons product stream 740 comprises $C_{5+}$ hydrocarbons. As will be appreciated by one of skill in the art, and with the help of this disclosure, the $C_{5+}$ hydrocarbons of the balance hydrocarbons product stream 740 (i) exclude benzene; (ii) include $C_{5+}$ olefins; (iii) include $C_{7+}$ aromatics; and (iv) include $C_{5+}$ paraffins, iso-paraffins and naphthenes.

The third separating unit 700 can comprise any suitable separating unit that is configured to separate the steam cracker product stream 610, the pyrolysis gas stream 120, the first gas stream 220, or combinations thereof into streams 710, 720, 730, 740, and 750. For example, the third separating unit 700 can employ vapor-liquid separators, liquid-gas coalescers, distillation columns, selective adsorption units, selective absorption units, extractive distillation columns, and the like, or combinations thereof.

In some aspects, the pyrolysis unit 100 and the steam cracker 600 operate at about the same pressure. In such aspects, the pyrolysis gas stream 120 or any portion thereof can be introduced to the third separating unit 700 without the need for adjusting a pressure of the pyrolysis gas stream 120 to meet the pressure requirements of the third separating unit 700.

In some aspects, a process for producing cumene can comprise conveying at least a portion of the balance hydrocarbons product stream 740 to the pyrolysis unit 100. In other aspects, a process for producing cumene can comprise conveying at least a portion 740a of the balance hydrocarbons product stream to the hydroprocessing unit 200. As will be appreciated by one of skill in the art, and with the help of this disclosure, the balance hydrocarbons product stream 740 or any portion thereof cannot be fed to the steam cracker 600 because of the olefin content.

A process for producing cumene can comprise a step of introducing at least a portion of the pyrolysis gas stream 120 and/or at least a portion of the first gas stream 220 to the first separating unit 300 to produce a first propylene stream 310, a first $C_2$ and $C_4$ unsaturated stream 320, and a saturated gas stream 330, wherein the first propylene stream 310 comprises propylene, wherein the first $C_2$ and $C_4$ unsaturated stream 320 comprises ethylene and butylenes, and wherein the saturated gas stream 330 comprises hydrogen and $C_1$ to $C_4$ saturated hydrocarbons, as well as CO and $CO_2$.

The first separating unit 300 can be any suitable separating unit that is configured to separate the pyrolysis gas stream 120 and/or the first gas stream 220 into the first propylene stream 310, the first $C_2$ and $C_4$ unsaturated stream 320, and the saturated gas stream 330. For example, the first separating unit 300 can employ distillation columns, cryogenic distillation columns, extractive distillation columns, selective adsorption units, selective absorption units, and the like, or combinations thereof.

In some aspects, the process for producing cumene can further comprise recovering at least a portion of the ethylene from the first $C_2$ and $C_4$ unsaturated stream 320 and/or the second $C_2$ and $C_4$ unsaturated stream 710. An overall ethylene yield can be equal to or greater than about 8 wt. %, alternatively equal to or greater than about 10 wt. %, alternatively equal to or greater than about 12.5 wt. %, or alternatively equal to or greater than about 15 wt. %.

In an aspect, a process for producing cumene as disclosed herein can be characterized by an overall ethylene and butylene yield of equal to or greater than about 15 wt. %, alternatively equal to or greater than about 20 wt. %, alternatively equal to or greater than about 25 wt. %, or alternatively equal to or greater than about 30 wt. %.

A process for producing cumene can comprise a step of feeding at least a portion of the first $C_2$ and $C_4$ unsaturated stream 320 and/or at least a portion of the second $C_2$ and $C_4$ unsaturated stream 710 to the metathesis reactor 800 to produce a second propylene stream 810, wherein the metathesis reactor 800 comprises a metathesis catalyst, and wherein the second propylene stream 810 comprises propylene. Generally, olefin metathesis refers to a reaction that entails redistribution of olefin fragments by scission and regeneration of carbon-carbon double bonds, a process also known as transalkylidenation. Olefins Conversion Technology (OCT) of Lummus Technology provides an example of olefin metathesis for the conversion of ethylene and butylenes to propylene.

The metathesis reactor 800 can comprise any suitable metathesis reactor, such as a continuous flow reactor, a batch reactor, a fixed bed reactor, a fluidized bed reactor, a catalytic distillation column reactor, and the like, or combinations thereof. The metathesis reactor 800 can be operated at conditions suitable for ethylene and butylenes metathesis to propylene, such as temperatures of equal to or greater than about 50° C., alternatively equal to or greater than about 100° C., alternatively equal to or greater than about 150° C., or alternatively equal to or greater than about 200° C.; pressures of from about 1 psi to about 1,500 psi, alternatively from about 10 psi to about 1,000 psi, or alternatively from about 25 psi to about 500 psi; and WHSVs of from about 0.1 $hr^{-1}$ to about 100 $hr^{-1}$, alternatively from about 1 $hr^{-1}$ to about 50 $hr^{-1}$, or alternatively from about 5 $hr^{-1}$ to about 25 $hr^{-1}$.

Nonlimiting examples of metathesis catalysts suitable for use in the present disclosure include organometallic compounds, Schrock catalysts, molybdenum alkylidenes, tungsten alkylidenes, Grubbs' catalysts, ruthenium carbenoid complexes, ruthenium carbenoid complexes modified with a chelating isopropoxystyrene ligand, Hoveyda catalysts, diphenylalkylamino based catalysts, and the like, or combinations thereof.

A process for producing cumene can comprise a step of feeding at least a portion of the first $C_6$ aromatics stream 420 and/or at least a portion of the second $C_6$ aromatics stream 730, and at least a portion of the first propylene stream 310, at least a portion of the second propylene stream 810, at least a portion of the third propylene stream 720, or combinations thereof to the alkylation unit 500 to produce a cumene stream 510, wherein the alkylation unit 500 comprises an alkylation catalyst, and wherein the cumene stream 510 comprises cumene.

The alkylation unit 500 can comprise any reactor (e.g., alkylation reactor) suitable for alkylating benzene with propylene to produce cumene, such as a fixed bed reactor, a fluidized bed reactor, etc.

In some aspects, the alkylation unit 500 can be operated at low temperature (e.g., less than about 135° C.) and low pressure (e.g., less than about 0.4 MPa). Benzene and propylene can be contacted in the alkylation reactor with the alkylation catalyst to produce an alkylation reactor effluent, which comprises a mixture of alkylated benzenes (e.g., cumene or isopropylbenzene) and polyalkylated benzenes (e.g., polyisopropylbenzenes). The alkylation reactor effluent can be further introduced to a transalkylation reactor comprising a transalkylation catalyst, wherein the polyisopropylbenzenes are transalkylated to cumene in the presence of benzene, and wherein a transalkylation reactor effluent is recovered from the transalkylation reactor. The alkylation reactor effluent and/or the transalkylation reactor effluent can be further introduced to a distillation system, wherein the distillation system can be designed to recover a high purity cumene product. The distillation system can recover cumene, as well as separate and recycle unconverted benzene and polyisopropylbenzenes to the alkylation reactor and/or the transalkylation reactor. The alkylation catalyst and the transalkylation catalyst can be the same or different. Nonlimiting examples of alkylation catalyst and/or transalkylation catalysts suitable for use in the present disclosure include a zeolite, β-zeolite, zeolite Y, ZSM-12, MCM-22, mordenite, and the like, or combinations thereof. The cumene production process of Polimeri Europa and Lummus Technology provides an example of cumene production from propylene and benzene, with the use of a proprietary zeolite catalyst formulation, PBE-1.

In other aspects, the alkylation unit 500 can be operated at high temperature (e.g., equal to or greater than about 150° C.) and high pressure (e.g., equal to or greater than about 1 MPa). In such aspects, the alkylation catalyst can comprise a solid phosphoric acid based catalyst.

In an aspect, a process for producing cumene as disclosed herein can be characterized by an overall cumene yield of equal to or greater than about 20 wt. %, alternatively equal to or greater than about 25 wt. %, or alternatively equal to or greater than about 28 wt. %. For purposes of the disclosure herein, all yields are calculated and reported as a weight % (wt. %) of the total weight of the plastic feed, unless otherwise specified.

In an aspect, a process for producing cumene as disclosed herein can be characterized by an overall propylene yield of equal to or greater than about 30 wt. %, or alternatively equal to or greater than about 35 wt. %. For purposes of the disclosure herein, the overall propylene yield accounts for propylene recovered at any point from the process, for example via the first propylene stream 310, the second propylene stream 810, the third propylene stream 720, or combinations thereof. As will be appreciated by one of skill in the art, and with the help of this disclosure, in configurations where a metathesis reactor is employed, such as shown in FIGS. 1A and 1B, the production of propylene can generally exceed the needs of the akylation unit, and as such propylene can also be recovered as a high value product from the process. In some aspects, propylene can be recovered as unconverted propylene subsequent to benzene alkylation by propylene to form cumene.

In an aspect, a process for producing cumene as disclosed herein can be characterized by an overall propylene and cumene yield of equal to or greater than about 60 wt. %, or alternatively equal to or greater than about 65 wt. %.

In an aspect, a process for producing cumene as disclosed herein can be characterized by an overall propylene, cumene, and ethylene yield of equal to or greater than about 70 wt. %, or alternatively equal to or greater than about 75 wt. %.

In an aspect, a process for producing cumene as disclosed herein can be characterized by an overall ethylene, propylene, and butylene yield of equal to or greater than about 30 wt. %, alternatively equal to or greater than about 35 wt. %, or alternatively equal to or greater than about 40 wt. %.

In an aspect, a process for producing propylene and cumene can comprise (a) converting a plastic waste to a hydrocarbon liquid stream and a pyrolysis gas stream in a high severity pyrolysis unit at a temperature of equal to or greater than about 450° C. and/or in a low severity pyrolysis unit at a temperature of from about 300° C. to about 450° C.; (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons; (c) introducing at least a portion of the hydrocarbon product to a second separating unit to produce a first $C_6$ aromatics stream comprising benzene and a refined product, wherein the refined product comprises $C_5+$ hydrocarbons other than $C_6$ aromatic hydrocarbons, wherein the refined product comprises less than 1 wt. % olefins, based on the total weight of the refined product, wherein the refined product comprises one or more chloride compounds in an amount of less than about 10 ppmw chloride, based on the total weight of the refined product, and wherein the refined product is characterized by a boiling end point of less than about 370° C.; (d) feeding at least a portion of the refined product to a steam cracker to produce a steam cracker product, wherein an amount of olefins in the steam cracker product is greater than an amount of olefins in the refined product; (e) introducing at least a portion of the steam cracker product to a third separating unit to produce a second $C_6$ aromatics stream, a third propylene stream, a second $C_2$ and $C_4$ unsaturated stream, a $C_1$ to $C_4$ saturated gas stream and a balance hydrocarbons product, wherein the second $C_6$ aromatics stream comprises benzene, wherein the third propylene stream comprises propylene, wherein the second $C_2$ and $C_4$ unsaturated stream comprises ethylene and butylenes, and wherein the $C_1$ to $C_4$ saturated gas stream comprises hydrogen and $C_1$ to $C_4$ saturated hydrocarbons; (f) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons; (g) feeding at least a portion of the first $C_2$ and $C_4$ unsaturated stream and/or at least a portion of the second $C_2$ and $C_4$ unsaturated stream to a metathesis reactor to produce a second propylene stream comprising propylene, wherein the metathesis reactor comprises a metathesis catalyst, and wherein the metathesis reactor is operated at a temperature of less than about 135° C. and a pressure of less than about 0.4 MPa; (h) feeding at least a portion of the first $C_6$ aromatics stream and/or at least a portion of the second $C_6$ aromatics stream, and at least a portion of the first propylene stream, at least a portion of the second propylene stream, at least a portion of the third propylene stream, or combinations thereof to an alkylation unit to produce cumene, wherein the alkylation unit comprises an alkylation catalyst, and wherein the alkylation catalyst comprises a zeolite; and (i) conveying at least a portion of the balance hydrocarbons product to the pyrolysis unit and/or the hydroprocessing unit. In such aspect, the process for producing propylene and cumene is characterized by an overall propylene and cumene yield of equal to or greater than about 60 wt. %.

In an aspect, a process for producing cumene can comprise (a) converting a plastic waste to a hydrocarbon liquid stream and a pyrolysis gas stream in a high severity pyrolysis unit at a temperature of equal to or greater than about 450° C. and/or in a low severity pyrolysis unit at a temperature of from about 300° C. to about 450° C.; (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons; (c) introducing at least a portion of the hydrocarbon product to a second separating unit to produce a first $C_6$ aromatics stream, a $C_{7-8}$ aromatics stream, and a saturated hydrocarbons stream, wherein the first $C_6$ aromatics stream comprises benzene, wherein the $C_{7-8}$ aromatics stream comprises toluene, xylenes and ethylbenzene, and wherein the saturated hydrocarbons stream comprises $C_5+$ saturated hydrocarbons; (d) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons; (h) feeding at least a portion of the first $C_6$ aromatics stream and at least a portion of the first propylene stream to an alkylation unit to produce cumene, wherein the alkylation unit comprises an alkylation catalyst, and wherein the alkylation catalyst comprises a zeolite; and (i) conveying at least a portion of the saturated hydrocarbons stream to the pyrolysis unit and/or the hydroprocessing unit. In such aspect, the process for producing cumene is characterized by an overall cumene yield of equal to or greater than about 25 wt. %, and by an overall ethylene and butylenes yield of equal to or greater than about 15 wt. %.

Processes for producing cumene as disclosed herein can advantageously display improvements in one or more process characteristics when compared to otherwise similar processes that do not employ processing plastic waste for producing both propylene and benzene, which can be further reacted to produce cumene. The processes for producing cumene as disclosed herein advantageously integrate pyrolysis, hydrocracking, olefin metathesis, and benzene alkylation to maximize production of cumene. The processes for producing cumene as disclosed herein can advantageously produce high value chemicals other than cumene, such as propylene, ethylene, butylenes, etc. Additional advantages of the process for producing cumene as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

High severity pyrolysis of mixed waste plastic was conducted to investigate the production of propylene and benzene for cumene synthesis. The mixed waste plastic had 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% was polyethylene terephthalate (PET). The pyrolysis was conducted in continuous catalytic cracking in circulating fluidized bed. The cracking was done with 57.5% spent fluid catalytic cracking (FCC) catalyst and with 42.5% ZSM-5 based zeolite additive and operated between 390-560° C. cup mix temperature of feed and catalyst. The feed rate of the plastic feed was 316 g/hr and the catalyst/feed weight ratio was about 30. In the case of a single stage pyrolysis process, the propylene content of the pyrolysis effluent was 23.7%, as it can be seen from the data in Table 1. The overall yield of light gas olefins was about 43 wt. %. The liquid product boiling below 240° C. had an aromatic concentration of 87.5 wt. %.

TABLE 1

| | Catalyst recipe 57.5.5% spent FCC catalyst + 42.5% ZSM5 zeolite catalyst High severity |
|---|---|
| Avg cup mix temp, [° C.] | 552.8 |
| Product yields, [wt. %] | |
| H2-C4 gas | 63.4 |
| Liquids | 32.7 |
| Coke | 3.9 |
| Ethylene | 8.65 |
| Propylene | 23.7 |
| Butylene | 10.9 |

In the case when a plastic feed was processed according to the process schematic displayed in FIGS. 1A and 1B, yields at various stages were calculated and are displayed in the table below:

| Compound | After Pyrolysis | After Pyrolysis and Hydroprocessing | After pyrolysis, hydroprocessing and steam cracking | After pyrolysis, hydrocracking, steam cracking and metathesis | After alkylation |
|---|---|---|---|---|---|
| Hydrogen | 0.12 | 0.12 | 0.53 | 0.53 | 0.53 |
| Methane | 0.54 | 1.16 | 7.03 | 7.03 | 7.03 |
| Acetylene | 0.00 | 0.00 | 0.14 | 0.14 | 0.14 |
| Ethylene | 8.65 | 8.65 | 19.72 | 13.93 | 13.93 |
| Ethane | 0.84 | 3.23 | 2.57 | 2.57 | 2.57 |
| Methylacetylene and Propadiene (MAPD) | 0.00 | 0.00 | 0.17 | 0.17 | 0.17 |
| Propylene | 23.73 | 23.73 | 28.17 | 45.54 | 35.40 |
| Propane | 4.93 | 6.33 | 0.70 | 0.70 | 0.70 |
| Butadiene | 0.00 | | 1.08 | 1.08 | 1.08 |

-continued

| Compound | After Pyrolysis | After Pyrolysis and Hydroprocessing | After pyrolysis, hydroprocessing and steam cracking | After pyrolysis, hydrocracking, steam cracking and metathesis | After alkylation |
|---|---|---|---|---|---|
| Butylene | 10.87 | 10.87 | 11.58 | 0.00 | 0.00 |
| Butanes | 12.12 | 13.52 | 0.70 | 0.70 | 0.70 |
| Pentanes | 0.00 | | | 0.00 | 0.00 |
| Benzene | 0.00 | 17.87 | 18.83 | 18.83 | 0.00 |
| Toluene | 0.00 | | 0.41 | 0.41 | 0.41 |
| Xylene | 0.00 | | 0.24 | 0.24 | 0.24 |
| C8H10 | 0.00 | | 0.06 | 0.06 | 0.06 |
| C6-C8 PON | 0.00 | | 0.00 | 0.00 | 0.00 |
| C6-200 GLN | 27.49 | 3.81 | 1.23 | 1.23 | 1.23 |
| FO | 5.20 | 5.20 | 1.33 | 1.33 | 1.33 |
| CO | 0.70 | 0.70 | 0.70 | 0.70 | 0.70 |
| CO2 | 0.93 | 0.93 | 0.93 | 0.93 | 0.93 |
| Propadiene | 0.00 | 0.00 | | 0.00 | 0.00 |
| Coke | 3.88 | 3.88 | 3.88 | 3.88 | 3.88 |
| Cumene | 0.00 | 0.00 | 0.00 | 0.00 | 28.97 |

Notes:
*In the case of pyrolysis (After Pyrolysis column): pentanes, benzene, toluene, xylene, C8H10, and C6-C8 PON (paraffins, olefins, naphthenes) yield values were already accounted in the C6-200 GLN yield value. C6-200 GLN refers to a gasoline cut from $C_6$ hydrocarbons to hydrocarbons boiling at 200° C., and includes all other hydrocarbons boiling in between the $C_6$ hydrocarbons and the hydrocarbons having a final boiling point of 200° C.
** FO accounts for heavies boiling >200° C.

In the case when a plastic feed was processed according to the process schematic displayed in FIG. 2, yields at various stages were calculated and are displayed in the table below:

| Compound | After Pyrolysis | After Pyrolysis and Hydroprocessing | After Alkylation |
|---|---|---|---|
| Hydrogen | 0.12 | 0.12 | 0.12 |
| Methane | 0.54 | 1.16 | 1.16 |
| Acetylene | 0.00 | 0.00 | 0.00 |
| Ethylene | 8.65 | 8.65 | 8.65 |
| Ethane | 0.84 | 3.23 | 3.23 |
| MAPD | 0.00 | 0.00 | 0.00 |
| Propylene | 23.73 | 23.73 | 14.10 |
| Propane | 4.93 | 6.33 | 6.33 |
| Butadiene | 0.00 | | 0.00 |
| Butylene | 10.87 | 10.87 | 10.87 |
| Butanes | 12.12 | 13.52 | 13.52 |
| Pentanes | 0.00 | | 0.00 |
| Benzene | 0.00 | 17.87 | 0.00 |
| Toluene | 0.00 | | 0.00 |
| Xylene | 0.00 | | 0.00 |
| C8H10 | 0.00 | | 0.00 |
| C6-C8 PON | 0.00 | | 0.00 |
| C6-200 GLN | 27.49 | 3.81 | 3.81 |
| FO | 5.20 | 5.20 | 5.20 |
| CO | 0.70 | 0.70 | 0.70 |
| CO2 | 0.93 | 0.93 | 0.93 |
| Propadiene | 0.00 | 0.00 | 0.00 |
| Coke | 3.88 | 3.88 | 3.88 |
| Cumene | 0.00 | 0.00 | 27.50 |

Notes:
*In the case of pyrolysis (After Pyrolysis column): pentanes, benzene, toluene, xylene, C8H10, and C6-C8 PON yield values were already accounted in the C6-200 GLN yield value.
** FO accounts for heavies boiling >200° C.

A pyrolysis oil recovered from the pyrolysis could be further fed to a hydrocracker. Gases would be cracked in gas steam crackers and liquids would be cracked in liquid steam crackers. The products would be separated. Ethylene and butylenes would then be subjected to metathesis to produce propylene. Propylene and benzene would then be reacted to produce a cumene product.

Example 2

Low severity pyrolysis of mixed waste plastic was conducted to investigate the production of propylene and benzene for cumene synthesis. The mixed waste plastic had 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% was polyethylene terephthalate (PET). The mixed plastic waste was pyrolyzed as described in Example 1, except for the temperature, which was about 450° C. A pyrolysis effluent was further hydrotreated to saturate all the liquid olefins, and then was further sent to steam cracking. A hydrotreated pyrolysis liquid can typically comprise 35-45% paraffins, 35-45% iso-paraffins, 15-20% naphthenes, and 5-10% aromatics, wherein the hydrotreated pyrolysis liquid boils below 400° C. The hydrotreated pyrolysis liquid could be subjected to (i) steam cracking alone; (ii) steam cracking followed by catalytic cracking with $C_4$-$C_5$ cracking; or (iii) catalytic cracking, and in each case different yields of propylene can be obtained, as it can be seen from Table 2.

TABLE 2

| Pyrolysis Outputs in wt % | Steam cracker product | steam cracker + catalytic cracker + C4, C5 cracking | catalytic cracking |
|---|---|---|---|
| Methane | 14.2 | 17.3 | 13.91 |
| Hydrogen | | | |
| Ethylene | 32.8 | 34.7 | 20.71 |
| Propylene | 17.8 | 24.6 | 22.06 |
| Butylenes | | | 8.97 |
| Saturates | 16.3 | | 19.78 |
| Gasoline | 14.5 | 20.5 | 13.58 |
| Diesel | 4.4 | 2.9 | 0.99 |

Example 3

A mixed plastic waste was cracked in modular units at low severity conditions; or catalytically cracked in a circulating fluidized bed at high severity; or catalytically cracked in a circulating fluidized bed at low severity to produce a pyrolysis oil. The results from these cracking experiments are shown below. The cup mix temperature was varied between 400-600° C., specifically 450-550° C. Depending on the severity of the operation, the gases and the liquid products were separated. The composition of the cracked liquid product is shown below in the tables. The saturated hydrocarbons present in the gas were sent to gas crackers which were an ethane cracker or propane cracker. The gas cracker was selected depending on the desired end product. The cracked liquid from the pyrolysis unit was sent to hydrotreating to saturate all the liquid olefins, as this is a requirement for the liquid/naphtha cracker. Hydrotreating was performed at 300-450° C. and at a pressure of 20-100 barg using commercially available hydrotreating catalyst to produce a hydrotreated oil. The typical composition of this hydrotreated oil was 35-45% paraffins, 35-45% iso-paraffins, 15-20% naphthenes and 5-10% aromatics, with a liquid boiling below 400° C. The table below shows an example of the composition of the hydrotreated oil (e.g., hydrocarbon product stream, such as stream 210). The hydrotreated oil was then subjected to steam cracking wherein the light gas olefins were maximized and the gas saturates formed were routed to a gas cracker. In this example, 16.3 wt. % saturates produced by pyrolysis were sent to the gas cracker to form more light gas olefins, such as ethylene and propylene.

The hydrotreated oil, normally a pygas, was naphtha range material with high aromatic content. This liquid can be subjected to aromatic extraction after mild hydrogenation and a non-aromatic stream can be sent back to the naphtha/steam cracker for further cracking.

The results for a saturated pyrolysis oil feed to the steam cracker having a composition of paraffins, olefins, naphthenes, and aromatics (P/O/N/A) are shown below.

|  | Catalyst recipe | | |
| --- | --- | --- | --- |
|  | 80% spent FCC catalyst + 20% ZSM-5 zeolite catalyst Low severity | 80% spent FCC catalyst + 20% ZSM-5 zeolite catalyst High severity | 65% spent FCC catalyst + 35% ZSM-5 zeolite catalyst High severity |
| Avg cup mix temp, ° C. | 452 | 521 | 553.9 |
| Product yields, wt. % | | | |
| H2-C4 gas | 47.90 | 55.1 | 61.6 |
| Liquids | 43.30 | 35.9 | 31.3 |
| Coke | 8.80 | 6.2 | 5.6 |
| Light gas olefins | 28.55 | 36.61 | 41.65 |
| Gas Saturates | 17.32 | 15.93 | 17.62 |
| Gasoline | 37.00 | 30.37 | 24.54 |
| Diesel | 5.31 | 4.43 | 5.36 |
| Heavies | 0.99 | 1.06 | 1.41 |
| Product composition of mixed plastic pyrolysis after cracking | Thermally cracked from modular technology unit | Catalytically cracked from circulating fluidized bed | |
| P |  | 45 | 9.5 |
| O |  | 34 | 4.2 |
| N |  | 11 | 3.6 |
| A |  | 9.4 | 82.7 |
| Product composition of mixed plastic pyrolyzed liquid after hydro treating | Thermally cracked from modular technology unit | Catalytically cracked from circulating fluidized bed | |
| P |  | 62 | 11.6 |
| O |  | 0 | 0.0 |
| N |  | 28.6 | 5.7 |
| A |  | 9.4 | 82.7 |

Depending on the composition for the pyrolysis liquid, whether it is from low severity catalytic cracking from continuous circulating fluidized bed or from thermal cracking from any modular technology, an aromatic extraction unit can be positioned before the steam cracker or after the steam cracker. If the aromatic content of the pyrolysis liquid is greater 40%, having the aromatic extraction before steam cracker could minimize the coke formation and also maximize recovery of high value chemicals like benzene, toluene, xylene and ethyl benzene before sending it to steam cracker.

The products obtained from the steam cracker are displayed below at steam-to-oil (S/O) ratio of 2 wt. %, a reaction residence time of 0.1 sec, and a temperature of 850° C. For purposes of the disclosure herein, the S/O ratio refers to the ratio expressed in mass percentage of the steam added to the steam cracker per total hydrocarbon feed of the steam cracker.

| Component | Steam cracker product [wt. %] |
| --- | --- |
| Methane | 14.2 |
| Hydrogen | |
| Ethylene | 32.8 |
| Propylene | 17.8 |
| Butylenes | |
| Saturates | 16.3 |
| Gasoline | 14.5 |
| Diesel | 4.4 |

Example 4

This example is related to low and high severity pyrolysis of mixed waste plastic having 82% olefinic feed (e.g., high-density polyethylene (HDPE), low-density polyethylene (LDPE), linear low-density polyethylene (LLDPE), and polypropylene (PP)); 11% polystyrene (PS); and the remaining 7% polyethylene terephthalate (PET). This experiment was conducted in a continuous catalytic cracking circulating fluidized bed. In all cases, the light gas olefins produced in the first step was greater than 28%, and saturates were also produced, which saturates can be sent directly to gas crackers to further increase the light gas olefins. The gasoline and diesel range material can be hydrotreated to saturate the liquid olefins and can be further sent to naphtha cracker. The overall make of light gas olefins combining the first stage pyrolysis followed by gas cracker for saturates and naphtha cracker for liquids can account for >60 wt. %, based on the total weight of the plastic feed (e.g., mixed waste plastic). Various catalyst recipes were tested according to the table below:

|  | Catalyst recipe | | |
| --- | --- | --- | --- |
|  | 80% spent FCC catalyst + 20% ZSM-5 zeolite catalyst Low severity | 80% spent FCC catalyst + 20% ZSM-5 zeolite catalyst High severity | 65% spent FCC catalyst + 35% ZSM-5 zeolite catalyst High severity |
| Avg cup mix temp. ° C. | 452 | 521 | 553.9 |
| Gas saturates feed to gas cracker | 17.32 | 15.93 | 17.62 |
| Gasoline saturates yield | 37.40 | 30.37 | 24.54 |
| C6-C8 aromatics concentration in liquid | 49.3 | 52.27 | 54.9 |

-continued

| | Catalyst recipe | | |
|---|---|---|---|
| | 80% spent FCC catalyst + 20% ZSM-5 zeolite catalyst Low severity | 80% spent FCC catalyst + 20% ZSM-5 zeolite catalyst High severity | 65% spent FCC catalyst + 35% ZSM-5 zeolite catalyst High severity |
| Gasoline saturates yields after C6-C8 aromatics separation | 18.96 | 14.50 | 11.07 |
| Diesel and heavies saturates yield | 6.30 | 5.49 | 6.77 |
| Diesel and Heavies saturates yield after hydroprocessing (calculated assuming complete saturation) | 6.69 | 5.83 | 7.19 |

The unconverted saturates can be recycled back to the cracker for further cracking and formation of light gas olefins. The pygas obtained from the naphtha cracker would be rich in aromatics which would be sent to aromatic extraction for separations of benzene, toluene, xylene (BTX) and ethylbenzene (EB) (BTX+EB).

Overall, by combining a pyrolyzer (e.g., pyrolysis unit) with a gas cracker and a liquid cracker, the high value chemicals like light gas olefins would be >60% and BTX+EB>15-20%.

Yields of liquid saturates in the gasoline and diesel range based on PIONA of pyrolysis oil would be sent to naphtha cracker for converting to high value chemicals. The $C_6$-$C_8$ range aromatics which are BTX+EB would be separated after hydrogenation. The higher aromatics which are normally di- and tri-aromatics would also be saturated or converted by ring opening and then a total feed consisting of gasoline saturates, diesel and heavies range saturates would be fed to the steam cracker to boost the overall yield of light gas olefins and BTX+EB range aromatics.

Overall, through the above examples, the processes involved in the process configuration of the integrated flowsheets as depicted in FIGS. 1-2 have been demonstrated to produce propylene and benzene that can be further used for the production of cumene.

The present disclosure is further illustrated by the following embodiments, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

The following are enumerated embodiments which are provided as non-limiting examples.

A first aspect, which is a process for producing propylene and cumene comprising (a) converting a plastic waste to a hydrocarbon liquid stream and a pyrolysis gas stream in a pyrolysis unit; (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_{5+}$ hydrocarbons; (c) introducing at least a portion of the hydrocarbon product to a second separating unit to produce a first $C_6$ aromatics stream and a refined product, wherein the refined product comprises $C_{5+}$ hydrocarbons other than $C_6$ aromatic hydrocarbons, and wherein the first $C_6$ aromatics stream comprises benzene; (d) feeding at least a portion of the refined product to a steam cracker to produce a steam cracker product, wherein an amount of olefins in the steam cracker product is greater than an amount of olefins in the refined product; (e) introducing at least a portion of the steam cracker product to a third separating unit to produce a second $C_6$ aromatics stream, a third propylene stream, a second $C_2$ and $C_4$ unsaturated stream, a $C_1$ to $C_4$ saturated gas stream and a balance hydrocarbons product, wherein the second $C_6$ aromatics stream comprises benzene, wherein the third propylene stream comprises propylene, wherein the second $C_2$ and $C_4$ unsaturated stream comprises ethylene and butylenes, and wherein the $C_1$ to $C_4$ saturated gas stream comprises hydrogen and $C_1$ to $C_4$ saturated hydrocarbons; (f) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons; (g) feeding at least a portion of the first $C_2$ and $C_4$ unsaturated stream and/or at least a portion of the second $C_2$ and $C_4$ unsaturated stream to a metathesis reactor to produce a second propylene stream, wherein the metathesis reactor comprises a metathesis catalyst, and wherein the second propylene stream comprises propylene; (h) feeding at least a portion of the first $C_6$ aromatics stream and/or at least a portion of the second $C_6$ aromatics stream, and at least a portion of the first propylene stream, at least a portion of the second propylene stream, at least a portion of the third propylene stream, or combinations thereof to an alkylation unit to produce cumene, wherein the alkylation unit comprises an alkylation catalyst; and (i) conveying at least a portion of the balance hydrocarbons product to the pyrolysis unit and/or the hydroprocessing unit.

A second aspect, which is the process of the first aspect, wherein the step (a) of converting a plastic waste to a hydrocarbon liquid stream and a pyrolysis gas stream in a pyrolysis unit is performed in a high severity pyrolysis unit at a temperature of equal to or greater than about 450° C. and/or in a low severity pyrolysis unit at a temperature of from about 300° C. to about 450° C.

A third aspect, which is the process of any one of the first and the second aspects, wherein the hydroprocessing catalyst comprises cobalt and molybdenum on an alumina support, nickel and molybdenum on an alumina support, tungsten and molybdenum on an alumina support, cobalt and molybdenum oxides on an alumina support, nickel and molybdenum oxides on an alumina support, tungsten and molybdenum oxides on an alumina support, cobalt and molybdenum sulphides on an alumina support, nickel and molybdenum sulphides on an alumina support, tungsten and molybdenum sulphides on an alumina support, a zeolite comprising one or more metals, or combinations thereof.

A fourth aspect, which is the process of the third aspect, wherein each metal of the one or more metals can be selected from the group consisting of cobalt, molybdenum, tungsten, nickel, titanium, copper, magnesium, tin, iron, zinc, tungsten, vanadium, gallium, calcium, manganese, ruthenium and rhenium; and wherein the zeolite comprises ZSM-5, ZSM-11, Y, high-silica Y, USY, or combinations thereof.

A fifth aspect, which is the process of any one of the first through the fourth aspects, wherein the step (b) of contacting at least a portion of the hydrocarbon liquid stream with a hydroprocessing catalyst is performed at a temperature of from about 250° C. to about 600° C.

A sixth aspect, which is the process of any one of the first through the fifth aspects, wherein the step (b) of contacting at least a portion of the hydrocarbon liquid stream with a hydroprocessing catalyst is performed at a pressure of from about 1 barg to about 200 barg.

A seventh aspect, which is the process of any one of the first through the sixth aspects, wherein the hydrocarbon product comprises equal to or greater than about 90 wt. % $C_{10}-$ hydrocarbons, based on the total weight of the hydrocarbon product.

An eighth aspect, which is the process of any one of the first through the seventh aspects, wherein the hydrocarbon product comprises less than about 1 wt. % olefins, based on the total weight of the hydrocarbon product.

A ninth aspect, which is the process of any one of the first through the eighth aspects, wherein the hydrocarbon product further comprises one or more chloride compounds in an amount of less than about 10 ppmw chloride, based on the total weight of the hydrocarbon product.

A tenth aspect, which is the process of any one of the first through the ninth aspects, wherein the hydrocarbon product is characterized by a boiling end point of less than about 370° C.

An eleventh aspect, which is the process of any one of the first through the tenth aspects, wherein the step (a) of converting a plastic waste to a hydrocarbon liquid stream and a pyrolysis gas stream in a pyrolysis unit and the step (d) of feeding at least a portion of the refined product to a steam cracker to produce a steam cracker product are performed at about the same pressure.

A twelfth aspect, which is the process of the eleventh aspect further comprising conveying at least a portion of the pyrolysis gas stream to the third separating unit.

A thirteenth aspect, which is the process of any one of the first through the twelfth aspects further comprising conveying at least a portion of the first gas stream to the third separating unit.

A fourteenth aspect, which is the process of any one of the first through the thirteenth aspects, wherein the metathesis catalyst comprises organometallic compounds, Schrock catalysts, molybdenum alkylidenes, tungsten alkylidenes, Grubbs' catalysts, ruthenium carbenoid complexes, ruthenium carbenoid complexes modified with a chelating isopropoxystyrene ligand, Hoveyda catalysts, diphenylalkylamino based catalysts, or combinations thereof.

A fifteenth aspect, which is the process of any one of the first through the fourteenth aspects, wherein the alkylation catalyst comprises a zeolite, β-zeolite, zeolite Y, ZSM-12, MCM-22, mordenite, or combinations thereof.

A sixteenth aspect, which is the process of any one of the first through the fifteenth aspects, wherein an overall propylene and cumene yield is equal to or greater than about 60 wt. %.

A seventeenth aspect, which is the process of any one of the first through the sixteenth aspects, wherein an overall propylene yield is equal to or greater than about 30 wt. %.

An eighteenth aspect, which is the process of any one of the first through the seventeenth aspects, wherein an overall propylene yield is equal to or greater than about 35 wt. %.

A nineteenth aspect, which is the process of any one of the first through the eighteenth aspects, wherein an overall cumene yield is equal to or greater than about 20 wt. %.

A twentieth aspect, which is the process of any one of the first through the nineteenth aspects, wherein an overall cumene yield is equal to or greater than about 28 wt. %.

A twenty-first aspect, which is the process of any one of the first through the twentieth aspects, wherein the pyrolysis gas stream and/or the first gas stream comprise $C_1$ to $C_4$ hydrocarbons and hydrogen.

A twenty-second aspect, which is the process of any one of the first through the twenty-first aspects further comprising conveying at least a portion of the balance hydrocarbons product to the hydroprocessing unit.

A twenty-third aspect, which is a process for producing cumene comprising (a) converting a plastic waste to a hydrocarbon liquid stream and a pyrolysis gas stream in a pyrolysis unit; (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons; (c) introducing at least a portion of the hydrocarbon product to a second separating unit to produce a first $C_6$ aromatics stream, a $C_{7-8}$ aromatics stream, and a saturated hydrocarbons stream, wherein the first $C_6$ aromatics stream comprises benzene, wherein the $C_{7-8}$ aromatics stream comprises toluene, xylenes and ethylbenzene, and wherein the saturated hydrocarbons stream comprises $C_5+$ saturated hydrocarbons and $C_{9+}$ aromatic hydrocarbons; (d) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons; (h) feeding at least a portion of the first $C_6$ aromatics stream and at least a portion of the first propylene stream to an alkylation unit to produce cumene, wherein the alkylation unit comprises an alkylation catalyst; and (i) conveying at least a portion of the saturated hydrocarbons stream to the pyrolysis unit and/or the hydroprocessing unit.

A twenty-fourth aspect, which is the process of the twenty-third aspect, wherein the pyrolysis unit is a high severity pyrolysis unit.

A twenty-fifth aspect, which is the process of any one of the twenty-third and the twenty-fourth aspects, wherein an overall cumene yield is equal to or greater than about 20 wt. %, and wherein an overall ethylene, propylene, and butylenes yield is equal to or greater than about 30 wt. %.

A twenty-sixth aspect, which is the process of any one of the twenty-third through the twenty-fifth aspects further comprising recovering at least a portion of the xylenes from the $C_{7-8}$ aromatics stream.

A twenty-seventh aspect, which is the process of any one of the twenty-third through the twenty-sixth aspects further comprising recovering at least a portion of the ethylene from the first $C_2$ and $C_4$ unsaturated stream.

A twenty-eighth aspect, which is the process of the twenty-seventh aspect, wherein an overall ethylene yield is equal to or greater than about 8 wt. %.

A twenty-ninth aspect, which is the process of any one of the twenty-third through the twenty-eighth aspects further comprising conveying at least a portion of the saturated hydrocarbons stream to the hydroprocessing unit.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing propylene and cumene comprising:
   (a) converting a plastic waste to a hydrocarbon liquid stream and a pyrolysis gas stream in a pyrolysis unit;
   (b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons;
   (c) introducing at least a portion of the hydrocarbon product to a second separating unit to produce a first $C_6$ aromatics stream and a refined product, wherein the refined product comprises $C_{5+}$ hydrocarbons other than $C_6$ aromatic hydrocarbons, and wherein the first $C_6$ aromatics stream comprises benzene;
   (d) feeding at least a portion of the refined product to a steam cracker to produce a steam cracker product, wherein an amount of olefins in the steam cracker product is greater than an amount of olefins in the refined product;
   (e) introducing at least a portion of the steam cracker product to a third separating unit to produce a second $C_6$ aromatics stream, a third propylene stream, a second $C_2$ and $C_4$ unsaturated stream, a $C_1$ to $C_4$ saturated gas stream and a balance hydrocarbons product, wherein the second $C_6$ aromatics stream comprises benzene, wherein the third propylene stream comprises propylene, wherein the second $C_2$ and $C_4$ unsaturated stream comprises ethylene and butylenes, and wherein the $C_1$ to $C_4$ saturated gas stream comprises hydrogen and $C_1$ to $C_4$ saturated hydrocarbons;
   (f) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons;
   (g) feeding at least a portion of the first $C_2$ and $C_4$ unsaturated stream and/or at least a portion of the second $C_2$ and $C_4$ unsaturated stream to a metathesis reactor to produce a second propylene stream, wherein the metathesis reactor comprises a metathesis catalyst, and wherein the second propylene stream comprises propylene;
   (h) feeding at least a portion of the first $C_6$ aromatics stream and/or at least a portion of the second $C_6$ aromatics stream, and at least a portion of the first propylene stream, at least a portion of the second propylene stream, at least a portion of the third propylene stream, or combinations thereof to an alkylation unit to produce cumene, wherein the alkylation unit comprises an alkylation catalyst; and
   (i) conveying at least a portion of the balance hydrocarbons product to the pyrolysis unit and/or the hydroprocessing unit.

2. The process of claim 1, wherein the step (a) of converting a plastic waste to a hydrocarbon liquid stream and a pyrolysis gas stream in a pyrolysis unit is performed at a temperature of equal to or greater than about 450° C.

3. The process of claim 1, wherein the hydroprocessing catalyst comprises cobalt and molybdenum on an alumina support, nickel and molybdenum on an alumina support, tungsten and molybdenum on an alumina support, cobalt and molybdenum oxides on an alumina support, nickel and molybdenum oxides on an alumina support, tungsten and molybdenum oxides on an alumina support, cobalt and molybdenum sulphides on an alumina support, nickel and molybdenum sulphides on an alumina support, tungsten and molybdenum sulphides on an alumina support, a zeolite comprising one or more metals, or combinations thereof.

4. The process of claim 3, wherein each metal of the one or more metals can be selected from the group consisting of cobalt, molybdenum, tungsten, nickel, titanium, copper, magnesium, tin, iron, zinc, tungsten, vanadium, gallium, calcium, manganese, ruthenium and rhenium; and wherein the zeolite comprises ZSM-5, ZSM-11, Y, high-silica Y, USY, or combinations thereof.

5. The process of claim 1, wherein the step (b) of contacting at least a portion of the hydrocarbon liquid stream with a hydroprocessing catalyst is performed at a temperature of from about 250° C. to about 600° C.

6. The process of claim 1, wherein the step (b) of contacting at least a portion of the hydrocarbon liquid stream with a hydroprocessing catalyst is performed at a pressure of from about 1 barg to about 200 barg.

7. The process of claim 1, wherein the hydrocarbon product (1) comprises equal to or greater than about 90 wt. % $C_{10}$-hydrocarbons, based on the total weight of the hydrocarbon product; (2) comprises less than about 1 wt. % olefins, based on the total weight of the hydrocarbon product; (3) further comprises one or more chloride compounds in an amount of less than about 10 ppmw chloride, based on the total weight of the hydrocarbon product; and (4) is characterized by a boiling end point of less than about 370° C.

8. The process of claim 1, wherein the step (a) of converting a plastic waste to a hydrocarbon liquid stream and a pyrolysis gas stream in a pyrolysis unit and the step (d) of feeding at least a portion of the refined product to a steam cracker to produce a steam cracker product are performed at about the same pressure.

9. The process of claim 8, further comprising conveying at least a portion of the pyrolysis gas stream to the third separating unit.

10. The process of claim 1, further comprising conveying at least a portion of the first gas stream to the third separating unit.

11. The process of claim 1, wherein the metathesis catalyst comprises organometallic compounds, Schrock catalysts, molybdenum alkylidenes, tungsten alkylidenes, Grubbs' catalysts, ruthenium carbenoid complexes, ruthenium carbenoid complexes modified with a chelating isopropoxystyrene ligand, Hoveyda catalysts, diphenylalkylamino based catalysts, or combinations thereof.

12. The process of claim 1, wherein the alkylation catalyst comprises a zeolite, β-zeolite, zeolite Y, ZSM-12, MCM-22, mordenite, or combinations thereof.

13. The process of claim 1, wherein an overall propylene and cumene yield is equal to or greater than about 60 wt. %.

14. The process of claim 11, wherein an overall propylene yield is equal to or greater than about 30 wt. %; and wherein an overall cumene yield is equal to or greater than about 20 wt. %.

15. The process of claim 1, wherein the pyrolysis gas stream and/or the first gas stream comprise $C_1$ to $C_4$ hydrocarbons and hydrogen.

16. The process of claim 1, further comprising conveying at least a portion of the balance hydrocarons product to the hydroprocessing unit.

17. A process for producing cumene comprising:
(a) converting a plastic waste to a hydrocarbon liquid stream and a pyrolysis gas stream in a pyrolysis unit;
(b) contacting at least a portion of the hydrocarbon liquid stream with a hydroprocessing catalyst in the presence of hydrogen in a hydroprocessing unit to yield a hydrocarbon product and a first gas stream, wherein the hydrocarbon product comprises $C_5+$ hydrocarbons;
(c) introducing at least a portion of the hydrocarbon product to a second separating unit to produce a first $C_6$ aromatics stream, a $C_{7-8}$ aromatics stream, and a saturated hydrocarbons stream, wherein the first $C_6$ aromatics stream comprises benzene, wherein the $C_{7-8}$ aromatics stream comprises toluene, xylenes and ethylbenzene, and wherein the saturated hydrocarbons stream comprises $C_5+$ saturated hydrocarbons and $C_{9+}$ aromatic hydrocarbons;
(d) introducing at least a portion of the pyrolysis gas stream and/or at least a portion of the first gas stream to a first separating unit to produce a first propylene stream, a first $C_2$ and $C_4$ unsaturated stream and a saturated gas stream, wherein the first propylene stream comprises propylene, wherein the first $C_2$ and $C_4$ unsaturated stream comprises ethylene and butylenes, and wherein the saturated gas stream comprises hydrogen and $C_1$ to $C_4$ saturated hydrocarbons;
(e) feeding at least a portion of the first $C_6$ aromatics stream and at least a portion of the first propylene stream to an alkylation unit to produce cumene, wherein the alkylation unit comprises an alkylation catalyst; and
(f) conveying at least a portion of the saturated hydrocarbons stream to the pyrolysis unit and/or the hydroprocessing unit.

18. The process of claim 17, wherein the pyrolysis unit is a high severity pyrolysis unit.

19. The process of claim 17, wherein an overall cumene yield is equal to or greater than about 20 wt. %, and wherein an overall ethylene, propylene, and butylenes yield is equal to or greater than about 30 wt. %.

20. The process of claim 17, further comprising (1) recovering at least a portion of the ethylene from the first $C_2$ and $C_4$ unsaturated stream; and/or (2) conveying at least a portion of the saturated hydrocarbons stream to the hydroprocessing unit.

* * * * *